(12) United States Patent
Mirica et al.

(10) Patent No.: US 9,422,286 B2
(45) Date of Patent: Aug. 23, 2016

(54) METAL-BINDING BIFUNCTIONAL COMPOUNDS AS DIAGNOSTIC AGENTS FOR ALZHEIMER'S DISEASE

(71) Applicant: Washington University, St. Louis, MO (US)

(72) Inventors: Liviu Mirica, University City, MO (US); Anuj Sharma, St. Louis, MO (US); Jason Schultz, Alexandria, MN (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 14/606,714

(22) Filed: Jan. 27, 2015

(65) Prior Publication Data

US 2015/0209452 A1    Jul. 30, 2015

Related U.S. Application Data

(60) Provisional application No. 61/932,011, filed on Jan. 27, 2014.

(51) Int. Cl.
| | |
|---|---|
| *C07D 471/18* | (2006.01) |
| *C07D 417/10* | (2006.01) |
| *C07F 1/00* | (2006.01) |
| *A61K 51/04* | (2006.01) |

(52) U.S. Cl.
CPC .......... *C07D 471/18* (2013.01); *A61K 51/0482* (2013.01); *A61K 51/0497* (2013.01); *C07D 417/10* (2013.01); *C07F 1/005* (2013.01)

(58) Field of Classification Search
CPC ........... A61K 49/0002; A61K 51/0453; A61K 49/0438; A61K 49/10; A61K 51/0474; C07D 277/66; C07D 307/79; C07D 307/80; C07D 307/81; C07D 307/82; C07D 405/04; C07D 407/04; C07D 409/04; C07D 413/04
See application file for complete search history.

(56) References Cited

U.S. PATENT DOCUMENTS

| | | | |
|---|---|---|---|
| 3,972,875 | A | 8/1976 | Smith |
| 7,727,511 | B2 | 6/2010 | Siclovan et al. |
| 8,147,798 | B2 | 4/2012 | Klunk et al. |
| 2009/0123373 | A1 | 5/2009 | Wang et al. |

FOREIGN PATENT DOCUMENTS

| | | | |
|---|---|---|---|
| WO | 2007003944 A2 | 1/2007 | |
| WO | 2008061306 A1 | 5/2008 | |
| WO | 2010063069 A1 | 6/2010 | |
| WO | 2010066010 A1 | 6/2010 | |
| WO | 2012051170 A2 | 4/2012 | |
| WO | 2013082655 A1 | 6/2013 | |
| WO | 2013082656 A1 | 6/2013 | |
| WO | 2013082661 A1 | 6/2013 | |
| WO | WO2013/082656 A1 * | 6/2013 | .......... C07D 487/08 |

OTHER PUBLICATIONS

Bottino, F., et al., "Reaction of tosylamide monosodium salt with bis(halomethyl) compounds: an easy entry to symmetrical N-tosyl aza macrocycles," 1988, J Org Chem, 53:3521-3529.
Dickson, D.W., "Neuropathological Diagnosis of Alzheimer's Disease: A Perspective from Longitudinal Clinicopathological Studies," 1997, Neurobiology of Aging, 18/4:S1-S106, Abstract.
Capule, C.C., "The design, synthesis, and evaluation of compounds that bind to Alzheimer's-related and HIV-1-related Amyloids," 2012, Theses and Dissertations, UC San Diego, 219 pages, <https://escholarship.org/uc/item/21x147vr>.
Hickey, J.L. et al., "Diagnostic Imaging Agents for Alzheimer's Disease: Copper Radiopharmaceuticals that Target Aβ Plaques," J. Am. Chem. Soc., 2013, 135 (43), pp. 16120-16132.
Khusnutdinova, J.R., et al., "Late First-Row Transition Metal Complexes of a Tetradentate Pyridinophane Ligand: Electronic Properties and Reactivity Implications," 2013, Inorg. Chem., 2013, 52 (7), pp. 3920-3932.
Johnson, K.A., et al., "Appropriate use criteria for amyloid PET: a report of the Amyloid Imaging Task Force, the Society of Nuclear Medicine and Molecular Imaging, and the Alzheimer's Association," Alzheimers Dement., Jan. 2013; 9(1):e-1-16.
Lockhart, A., et al., "Evidence for the presence of three distinct binding sites for the thioflavin T class of Alzheimer's disease PET imaging agents on beta-amyloid peptide fibrils," J Biol Chem. Mar. 4, 2005;280(9):7677-84.
Meneghetti, S. P., et al., "Neutral and Cationic Palladium(II) Complexes of a Diazapyridinophane. Structure, Fluxionality, and Reactivity toward Ethylene," Organometallics, 2001, 20 (24), pp. 5050-5055.
Mirica, L.M., et al., "Structure and electronic properties of Pd(III) complexes," Coordination Chem Reviews, Jan. 15, 2013, vol. 257, Issue 2, pp. 299-314.
Hit2Lead Search Result for 4-(1,3-benzothiazol-2-yl)-2-({benzyl[2-(dimethylamino)ethyl]amino} methyl)phenol, <http://www.hit2lead.com/result.asp?search=15031162>, retrieved May 6, 2013, 1 page.
Goldsbury et al., "Amyloid fibril formation from full-length and fragments of amylin," J. Struct. Biol., Jun. 2000, 130(2-3), pp. 352-362.
Nordberg, A., "Amyloid imaging in Alzheimer's disease," Neuropsychologia, 2008;46(6):1636-41.
Sharma, A.K., et al., "Bifunctional compounds for controlling metal-mediated aggregation of the 442 peptide," J Am Chem Soc. Apr. 18, 2012;134(15):6625-36.
Sharma, A.K., et al., "The effect of Cu2+ and Zn2+ on the Aβ42 peptide aggregation and cellular toxicity," Metallomics, 2013,5, 1529-1536.
Missouri Inorganic Day, Poster Presentation, May 8, 2010, St. Louis University, Department of Chemistry, 34 pages.
(Continued)

*Primary Examiner* — Audrea Buckley
(74) *Attorney, Agent, or Firm* — Senniger Powers LLP

(57) ABSTRACT

Metal-binding bifunctional compounds and their use as diagnostic agents for Alzheimer's disease and other beta amyloid disorders are disclosed. Also, radiolabeled metal complexes of these bifunctional compounds and their use as positron emission tomography (PET) imaging agents are provided.

19 Claims, 13 Drawing Sheets

(56) References Cited

OTHER PUBLICATIONS

Zeman et al., "Diagnosis of Dementia Using Nuclear Medicine Imaging Modalities," 12 Chapters on Nuclear Medicine, Dr. Ali Gholamrezanezhad (Ed.), InTech, 2011, 33 pages, <http://cdn.intechopen.com/pdfs-wm/25572.pdf>.

Alderighi et al., "Hyperquad simulation and speciation (HySS): a utility program for the investigation of equilibria involving soluble and partially soluble species," Coordination Chemistry Reviews, vol. 184, Issue 1, Apr. 1999, pp. 311-318.

Esteves et al., "Remarkable inertness of copper(II) chelates of cyclen-based macrobicycles with two trans-N-acetate arms," Inorg. Chem. 2013, 52, pp. 5138-5153.

Klein, W. L., "Aβ toxicity in Alzheimer's disease: globular oligomers (ADDLs) as new vaccine and drug targets," Neurochemistry International, 2002, 41, pp. 345-352.

Roger et al., "Monopicolinate-dipicolyl derivative of triazacyclononane for stable complexation of Cu2+ and 64Cu2+," Inorganic Chemistry, 2013, 52(9), pp. 5246-5259.

Sheldrick, G. M., "A short history of SHELX", Acta Crystallographica, 2008, Section A, vol. 64, pp. 112-122.

Gans et al., "Determination of Equilibrium Constants from Spectrophometric Data Obtained from Solutions of known pH: The Program pHab", Annali di Chimica, 1999, 89, pp. 45-49.

Zhuang et al., "Radioiodinated styrylbenzenes and thioflavins as probes for amyloid aggregates," J Med Chem. Jun. 7, 2001, 44(12), pp. 1905-1194, Abstract.

Maltby, P., "Radiopharmacy quality control", 2009, 5 pages, <http://www.eanm.org/education_esnm/cme_cte/cte_2009/pdf/cte6c_maltby.pdf>.

Snm, "Non-Standard PET Radionuclides in Molecular Imaging," mi-gateway, 2012, vol. 6 Issue 2, 8 pages, <http://interactive.snm.org/docs/Issue2_2012GatewayWeb.pdf>.

Kung et al., "IMPY: an improved thioflavin-T derivative for in vivo labeling of β-amyloid plaques" Brain Research, 2002, vol. 956, Issue 2, Nov. 29, 2002, pp. 202-210.

Mathis et al., "Synthesis and evaluation of 11C-labeled 6-substituted 2-arylbenzothiazoles as amyloid imaging agents," J Med Chem., Jun. 2003, 19;46(13), pp. 2740-2754, Abstract.

Yadav et al., "Benzothiazole: Different Methods of Synthesis and Diverse Biological Activities," International Journal of Pharmaceutical Sciences and Drug Research, 2011, 3(1), pp. 1-7.

Weiner et al., "The Alzheimer's Disease Neuroimaging Initiative: a review of papers published since its inception" Alzheimers Dement., 2012, 8(10):S1-68, 115 pages.

Bradshaw et al., "The discovery of the potent and selective antitumour agent 2-(4-amino-3-methylphenyl) benzothiazole (DF 203) and related compounds," Current Medicinal Chemistry, 2001, 8(2), pp. 203-210.

* cited by examiner

FIG. 2
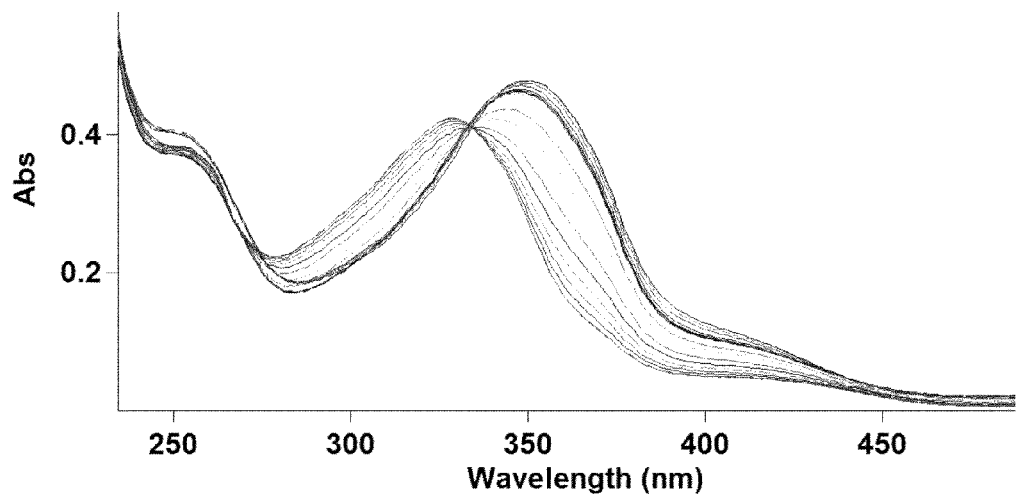
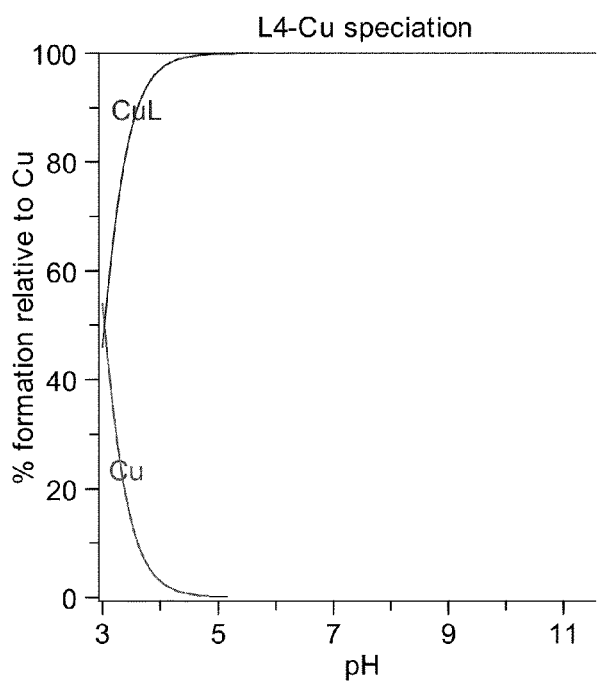

FIG. 5
(a)
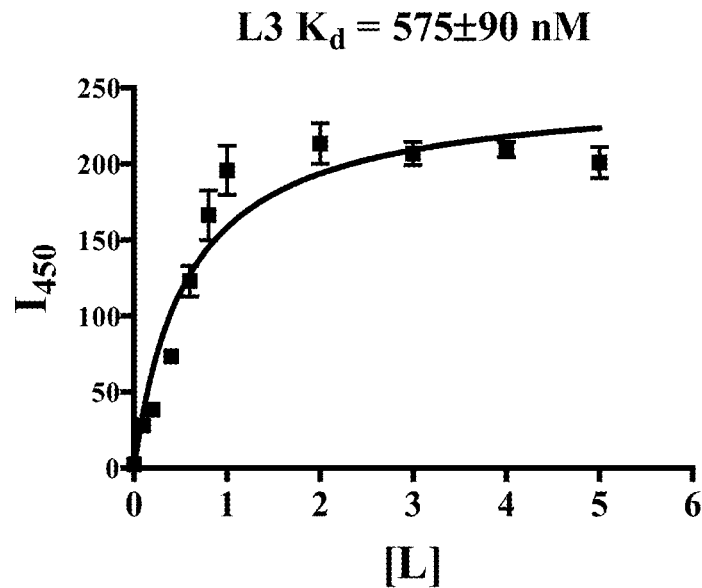
(b)
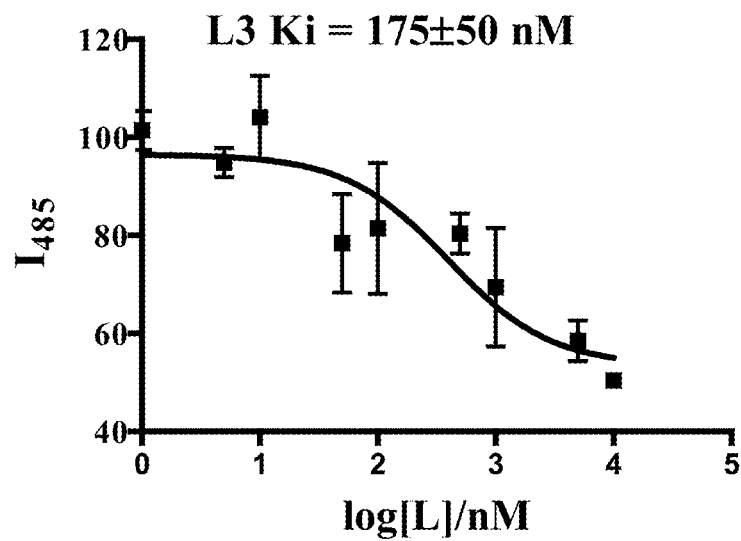

FIG. 6
(a)
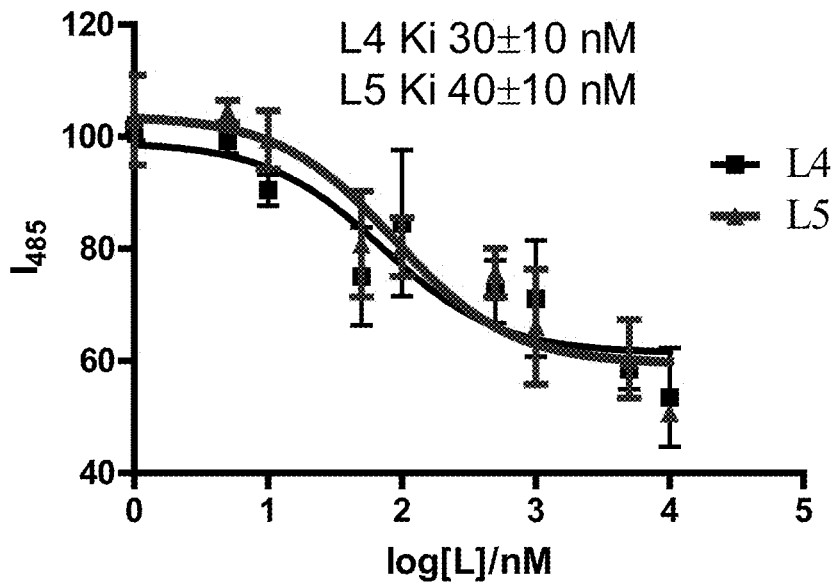
(b)
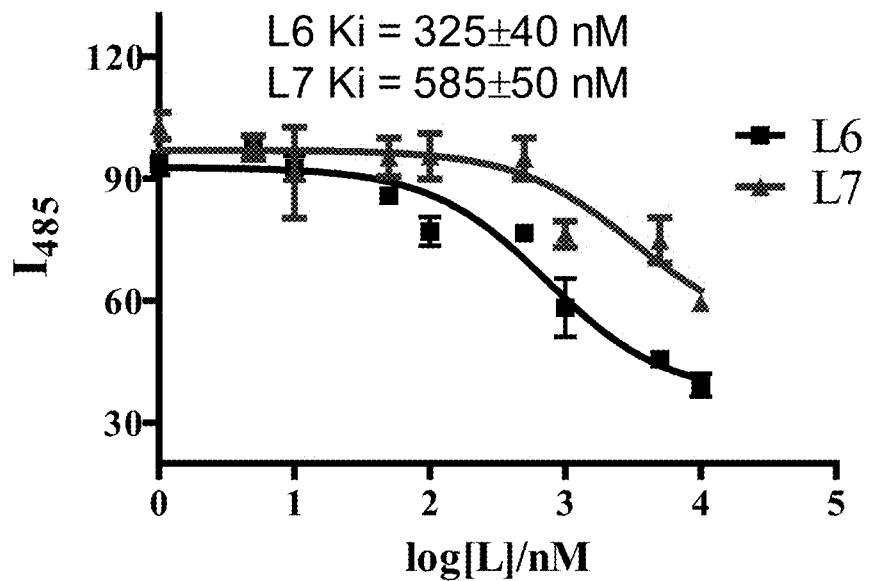

US 9,422,286 B2

METAL-BINDING BIFUNCTIONAL COMPOUNDS AS DIAGNOSTIC AGENTS FOR ALZHEIMER'S DISEASE

REFERENCE TO RELATED APPLICATIONS

This application claims benefit of U.S. provisional application Ser. No. 61/932,011, filed Jan. 27, 2014, the entire disclosure of which is incorporated herein by reference.

GOVERNMENT LICENSE RIGHTS

This invention was made with Government support under grant P50-AG05681, Washington University Knight Alzheimer's Disease Research Center Pilot Grant awarded by the National Institute of Aging of the National Institute of Health. The Government has certain rights in the invention.

FIELD OF THE INVENTION

The present invention generally relates to metal-binding bifunctional compounds and their use as diagnostic agents for Alzheimer's disease and other beta amyloid disorders. The invention further relates radiolabeled metal complexes of these bifunctional compounds and their use as positron emission tomography (PET) imaging agents.

BACKGROUND OF THE INVENTION

Alzheimer's disease (AD) is an irreversible, progressive neurodegenerative disease that slowly destroys memory and thinking skills, and eventually causes senile dementia. More than 5 million people in the U.S. and 24 million people worldwide suffer from this disease. The pathogenesis of AD is far from being understood, and 42- and 40-amino acids long amyloid β peptides ($A\beta_{42}$ and $A\beta_{40}$, respectively) are proposed to play a central role in the onset of AD. Although $A\beta_{40}$ is present in larger amounts in the brain, $A\beta_{42}$ was found to be more neurotoxic and has a higher tendency to aggregate. The amyloid cascade hypothesis suggests the ultimate products of Aβ aggregation, the amyloid plaques, are responsible for neurodegeneration. However, recent in vivo studies have shown that soluble Aβ oligomers are more neurotoxic than amyloid plaques and most likely responsible for synaptic dysfunction and memory loss in AD (Sharma et al., Metallomics, 2013, 5: 1529-1536).

The development of effective treatments for AD has been hindered, in large part, by the lack of methods available to definitively diagnose AD in living patients. Although AD is routinely diagnosed clinically after a series of mental status tests and physical examination, it can only be confirmed by demonstrating that the pathologic hallmarks of AD-protein deposits and neurofibrillary tangles are present in the brain. Major neuropathology observations of postmortem examination of AD brains confirm the presence of AD through the detection of extracellular β-amyloid peptides and intracellular neurofibrillary tangles (NFT). NFTs derive from filaments of hyperphosphorylated tau proteins. The presence and severity of NTFs correlate with severity of dementia and cognitive impairment (Dickson, D. W., Neurobiology of Aging, 1997, 18(4): S21-S26). The presence of these deposits is typically confirmed post mortem through autopsy of the brain. Autopsied brain tissues are treated with histologic dyes, such as Thioflavin T (ThT) or Congo Red (CR), which have an affinity for and stain amyloid plaques. These dyes are limited to post mortem use because their inherent charges prevent them from crossing the blood brain barrier in vivo.

In 2002, a labeled derivative of Thioflavin T known as $^{11}$C-Pittsburgh Compound Blue ($^{11}$C-PiB) was developed at the University of Pittsburgh. $^{11}$C-PiB was the first PET agent to show success in clinical trials, and is now the most well-characterized and studied radiopharmaceutical for Aβ pathology. In vitro autoradiography studies have confirmed that $^{11}$C-PiB binds to aggregated, fibrillar Aβ deposits in the cortex, striatum, and cerebral vessel walls, but not to amorphous, cerebellar Aβ deposits. At nanomolar concentrations, however, $^{11}$C-PiB does not bind to free soluble amyloid, tau neurofibrillary tangles (NFTs), or Lewy bodies (Zeman et al., 12 Chapters on Nuclear Medicine, 2011: 199-230).

Routine clinical use of $^{11}$C-PiB is limited by the short half-life of the $^{11}$C radioisotope (20.4 min), which necessitates on-site synthesis and immediate use of $^{11}$C-PiB for PET scanning. As a result, Aβ PET tracers that are radiolabeled with fluorine-18, a radioisotope with a considerably longer half-life (110 minutes) than carbon-11, have been developed. Fluorine-18 labeled Aβ PET tracers do not require on-site cyclotrons for their production, thus allowing for a more widespread distribution of this imaging technology. Several $^{18}$F-labeled Aβ PET radiopharmaceuticals have been developed, including $^{18}$F-flutemetamol, $^{18}$F-florbetaben, $^{18}$F-florbetapir, and $^{18}$F-AZD4694 (also named $^{18}$F-NAV4694). One such compound, $^{18}$F-forbetapir, was approved by the U.S. Food and Drug Administration in April 2012. The structures of the five Aβ PET radiopharmaceuticals in use at multiple sites to image Alzheimer pathology in vivo are shown below.

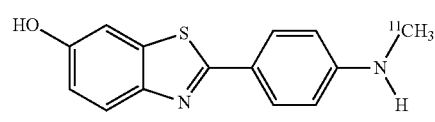

$^{11}$C-PiB

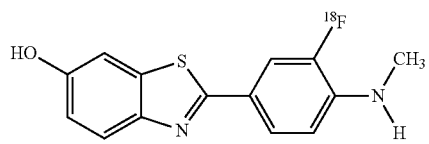

18F-flutemetamol

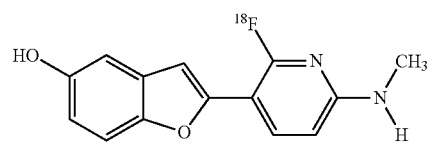

18F-AZD4694

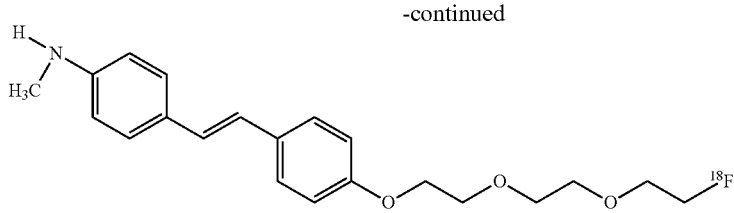

18F-florbetaben

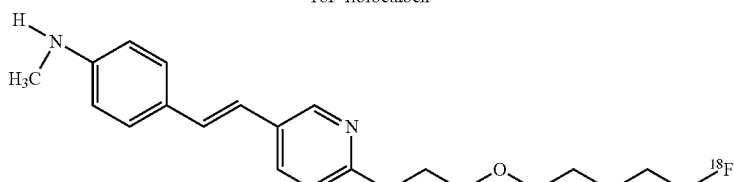

18F-florbetapir

Recently, Donnelly et al. reported the development of copper radiopharmaceuticals that target Aβ plaques for non-invasive diagnosis and monitoring of amyloid diseases (J. Am. Chem. Soc., 2013, 135:16120-16132). Initial attempts focused on derivatives of $Cu^{II}(astm)_2$, a known hypoxia imaging agent. It was found that bis(thiocarbazone) ligands were difficult to radiolabel with Cu-64 and that the thiocarbazone linkage was susceptible to hydrolysis. Subsequently, hybrid ligands ($Cu^{II}L^1$, $Cu^{II}L^2$, and $Cu^{II}L^3$) based on thiosemicarbazone-pyridylhydrazone were synthesized, and shown to form more stable, charge neutral $Cu^{II}$ complexes.

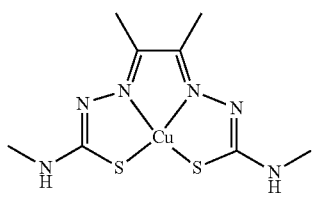

$Cu^{II}(atsm)$

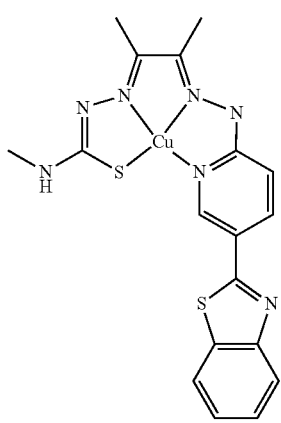

$Cu^{II}L^1$

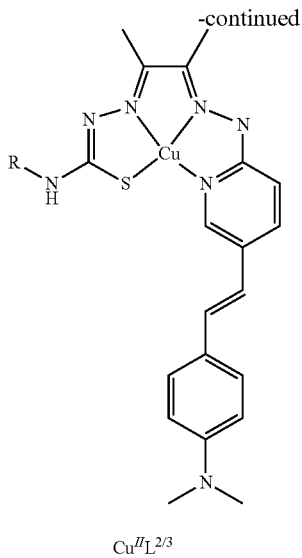

$Cu^{II}L^{2/3}$

Benzothiazole $^{11}C$-PiB was the structural inspiration behind the preparation of ligand ($H_2L^1$) for metal complex $Cu^{II}L^1$. Unfortunately, copper complex $Cu^{II}L^1$ suffered from very poor solubility and did not appear to selectively interact with human AD post-mortem brain tissue. In contrast, copper complexes $Cu^{II}L^2$ and $Cu^{II}L^3$ that incorporated a styrylpyridyl group instead of a benzothiazole group were found to bind to Aβ plaque. However, in preliminary biodistribution studies of copper-64 radiolabeled complexes of $Cu^{II}L^2$ and $Cu^{II}L^3$ in normal mice, only $Cu^{II}L^3$ crossed the blood-brain barrier. Thus, subtle differences in the ligand framework altered both the binding of the metal complex to Aβ plaque and its ability to enter the central nervous system.

The present inventors previously reported the synthesis of bifunctional chelators that contain amyloid binding and metal chelating motifs (Sharma et al., J. Am. Chem. Soc., 2012, 134: 6625-6636). Thus, bifunctional chelators L1 and L2 were designed with a 2-arylbenzothiazole moiety to enable binding to Aβ and an N-(2-pyridylmethyl) amine group to simultaneously chelate transition metals such as Cu, Zn, or Fe that have been found within amyloid deposits in AD brain tissue.

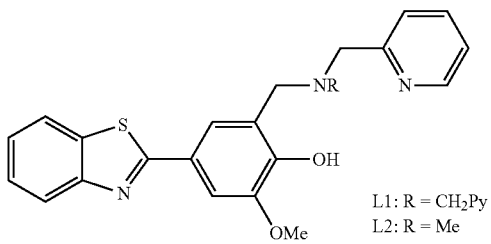

L1: R = CH$_2$Py
L2: R = Me

Both compounds L1 and L2 were found to be efficient inhibitors of the metal-mediated aggregation of the Aβ$_{42}$ peptide and promoted disaggregation of amyloid fibrils. However, the ability of L1 and L2 to inhibit Aβ fibril formation and promote fibril disaggregation led to increased cellular toxicity, especially for L2, limiting their potential as therapeutic agents.

There remains a need for improved imaging agents for the detection of Aβ species in Alzheimer's disease. Non-invasive functional molecular imaging techniques such as PET imaging have the potential to become the future diagnostic standard for Alzheimer's disease, as they would allow for earlier and more definitive diagnosis of such diseases and provide a more effective method for monitoring possible treatments. Thus, there is a need for nontoxic and longer-lived radiopharmaceutical compounds that bind selectively and with high affinity to various Aβ species, including β-amyloid plaques and neurofibrillary tangles.

SUMMARY OF THE INVENTION

In various aspects, the present invention is directed to compounds of Formula (I) or a pharmaceutically acceptable salt thereof:

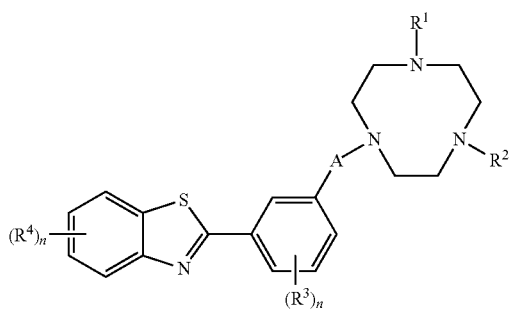

(I)

wherein $R^1$ and $R^2$ are each independently hydrogen, substituted or unsubstituted C$_1$-C$_4$ alkyl, substituted or unsubstituted aryl, substituted or unsubstituted heteroaryl, substituted or unsubstituted C$_1$-C$_4$ alkylcarboxy, substituted or unsubstituted C$_1$-C$_4$ alkylamide, substituted or unsubstituted C$_1$-C$_4$ alkylester, or a moiety of Formula (II):

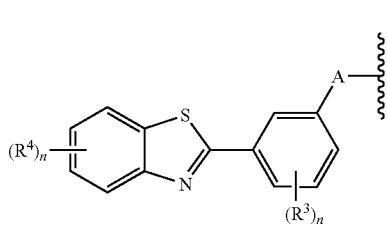

(II)

each $R^3$ and $R^4$ in Formulas (I) and (II) is independently hydroxy, halo, nitro, amino, substituted or unsubstituted C$_1$-C$_4$ alkyl, substituted or unsubstituted C$_1$-C$_4$ alkoxy, substituted or unsubstituted aryl, or substituted or unsubstituted heteroaryl;

each n in Formulas (I) and (II) is independently 0 to 4, 0 to 3, 0 to 2, 1, or 0; and each A in Formulas (I) and (II) is independently C$_1$-C$_4$ alkylene, carbonyl, amide, thioamide, sulfonamide, urea, or carbamate.

In other aspects, the present invention is directed to compounds of Formula (III) or a pharmaceutically acceptable salt thereof:

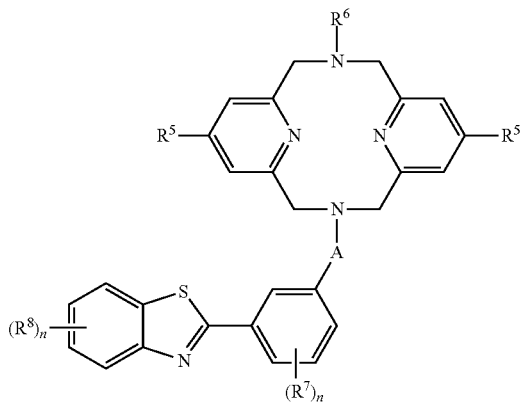

(III)

wherein each $R^5$ is independently hydrogen, hydroxy, halo, nitro, amino, substituted or unsubstituted C$_1$-C$_4$ alkyl, substituted or unsubstituted C$_1$-C$_4$ alkoxy, substituted or unsubstituted aryl, or substituted or unsubstituted heteroaryl;

$R^6$ is hydrogen, substituted or unsubstituted C$_1$-C$_4$ alkyl, substituted or unsubstituted aryl, substituted or unsubstituted heteroaryl, substituted or unsubstituted C$_1$-C$_4$ alkylcarboxy, substituted or unsubstituted C$_1$-C$_4$ alkylamide, substituted or unsubstituted C$_1$-C$_4$ alkylester, or a moiety of Formula (IV):

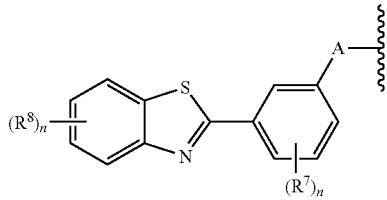

(IV)

each $R^7$ and $R^8$ of Formulas (III) and (IV) is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

each n in Formulas (III) and (IV) is independently 0 to 4, 0 to 3, 0 to 2, 1, or 0; and each A in Formulas (III) and (IV) is independently $C_1$-$C_4$ alkylene, carbonyl, amide, thioamide, sulfonamide, urea, or carbamate.

In various aspects, the present invention is directed compounds of Formula (V) or a pharmaceutically acceptable salt thereof:

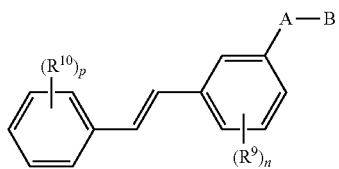

(V)

wherein
B is a moiety selected from the group consisting of:

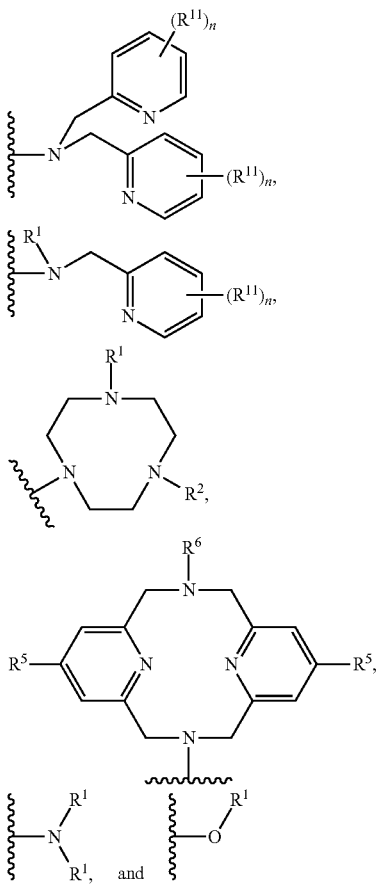

each $R^1$ and $R^2$ is independently hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester;

each $R^5$ is independently hydrogen, hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

$R^6$ is hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester, or a moiety of Formula (VI):

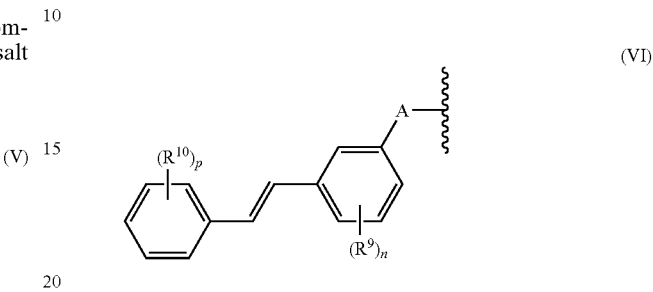

(VI)

each A in Formulas (V) and (VI) is independently $C_1$-$C_4$ alkylene, carbonyl, amide, thioamide, sulfonamide, urea, or carbamate;

each $R^9$ and $R^{10}$ in Formulas (V) and (VI) is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

each $R^{11}$ is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

each n is independently 0 to 4, 0 to 3, 0 to 2, 1, or 0; and
each p in Formulas (V) and (VI) is independently 0 to 5, 0 to 4, 0 to 3, 0 to 2, 1, or 0.

In further aspects, the present invention is directed to a metal radionuclide complex comprising a compound of Formulas (I), (III), or (V) and a metal radionuclide.

In yet other aspects, the present invention is directed to a method of diagnosing or monitoring a β-amyloid disease in a subject comprising:

administering a radiopharmaceutical composition comprising a diagnostically effective amount of a metal radionuclide complex of a compound of Formula (I), (III), or (V) to the subject; imaging the subject's brain by position emission tomography; and detecting the binding of the metal complex to Aβ species.

Other aspects of the invention will be in part apparent and in part pointed out hereinafter.

BRIEF DESCRIPTION OF THE DRAWINGS

FIG. 2 shows a variable pH (pH 3-11) UV-vis spectra of the L4-$Cu^{2+}$ system ([L4]=[$Cu^{2+}$]=50 μM, 25° C., I=0.1 M NaCl) and species distribution plot created by the program HYSS2009.

FIG. 5 shows a fluorescence assay of L3 with Aβ$_{40}$ fibrils ([Aβ]=5 μM) (graph (a)) and a ThT fluorescence competition assay of L3 with ThT-bound Aβ$_{40}$ fibrils ([Aβ]=2 μM, [ThT]=1 μM) (graph (b)).

FIG. 6 show a ThT fluorescence competition assay of L4-L7 with ThT-bound Aβ$_{40}$ fibrils ([Aβ]=2 μM, [ThT]=1 μM).

DESCRIPTION OF THE PREFERRED EMBODIMENTS

Figure 9:
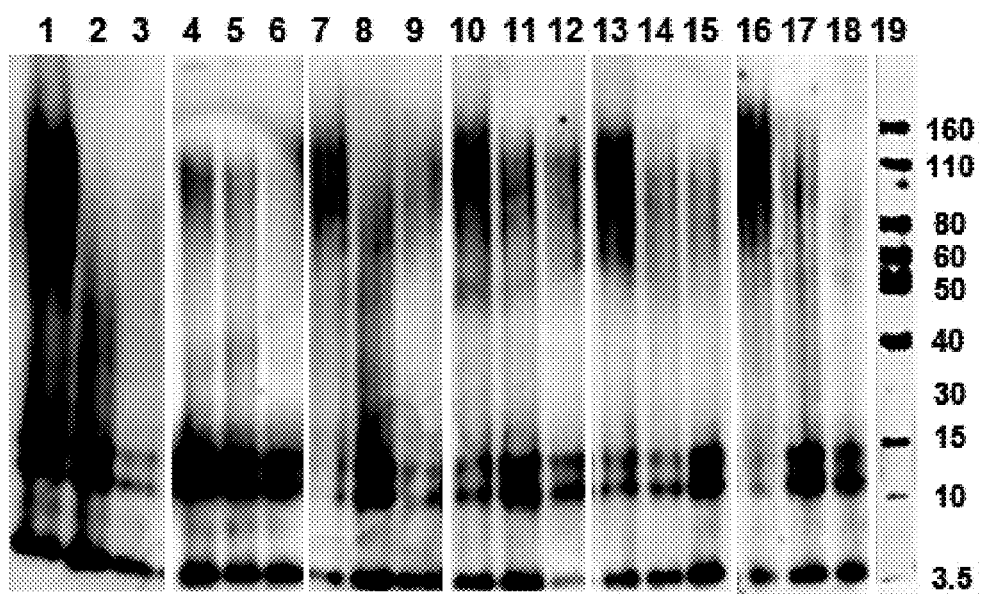
FIG. 9 shows a native gel/Western blot of Aβ species corresponding to inhibition experiments as described in FIGS. 7 and 8.

Generally, the present invention is directed to various compounds and methods of using these compounds for diagnostic imaging. In various aspects, the compounds are metal-binding bifunctional compounds that are useful in the preparation of radiolabeled metal complexes, which are effective radio imaging agents (e.g., PET imaging). It has been surprisingly discovered that various bifunctional compounds of the present invention that contain amyloid binding and metal chelating fragments do not lead to formation of soluble Aβ-oligomers (as shown in FIG. 9), and thus show limited cellular toxicity.

As noted, metal-binding bifunctional compounds of the present invention include an amyloid binding fragment and a metal chelating fragment, which can be represented by Formula (A):

B$^f$-C$^f$ (A)

where B$^f$ is the amyloid binding fragment and C$^f$ is the chelating fragment. As noted herein, the amyloid binding fragment includes compounds such as Thioflavin T and derivatives thereof (e.g., Formula (II)) and stilbene-phenol compounds and derivatives thereof (e.g., Formula (VI)). The metal chelating fragment includes, for example, a moiety selected from the group consisting of:

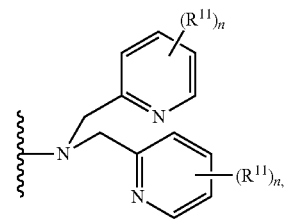

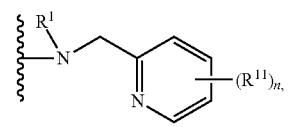

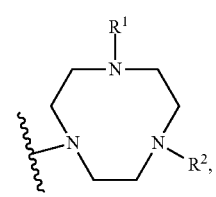

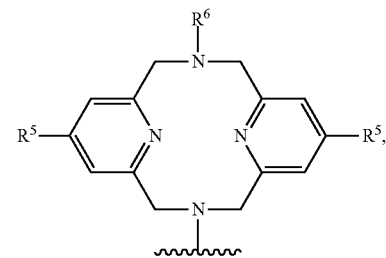

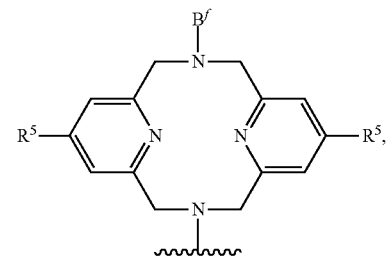

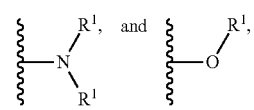

wherein R$^1$, R$^2$, R$^5$, R$^6$, R$^{11}$, and n are as defined herein.

In accordance various aspects of the present invention, metal-binding bifunctional compounds include compounds of Formula (I) or a pharmaceutically acceptable salt thereof:

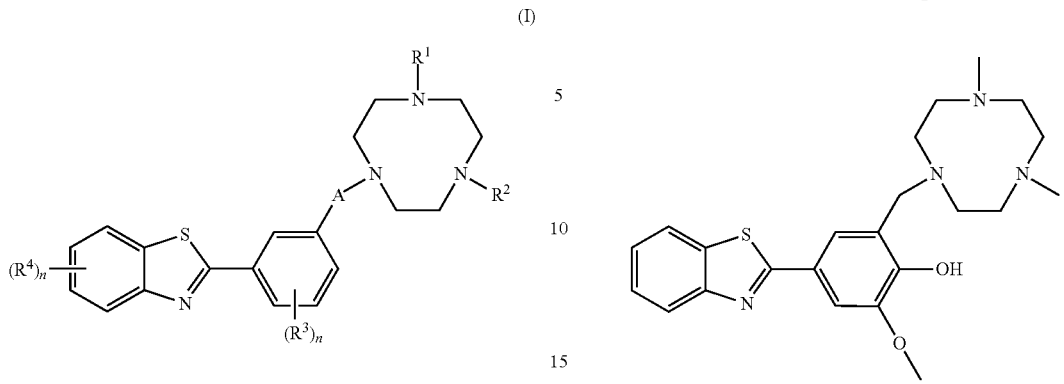

wherein

R¹ and R² are each independently hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester, or a moiety of Formula (II):

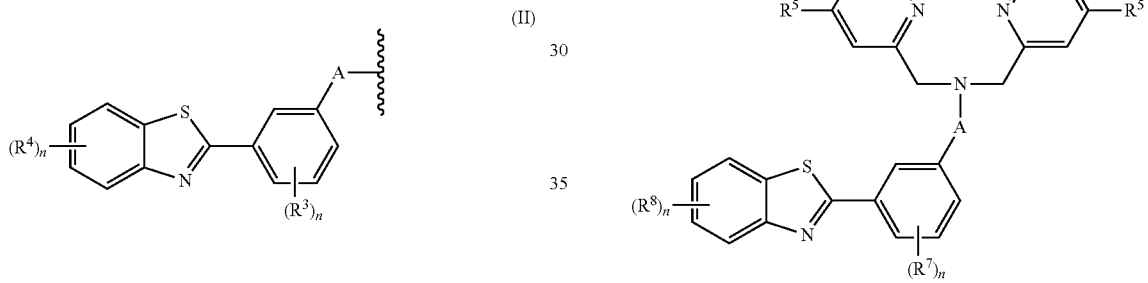

each R³ and R⁴ in Formulas (I) and (II) is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

each n in Formulas (I) and (II) is independently 0 to 4, 0 to 3, 0 to 2, 1, or 0; and each A in Formulas (I) and (II) is independently $C_1$-$C_4$ alkylene, carbonyl, amide, thioamide, sulfonamide, urea, or carbamate.

In various embodiments, R¹ and R² are each independently hydrogen, unsubstituted $C_1$-$C_4$ alkyl, unsubstituted aryl, unsubstituted heteroaryl, unsubstituted $C_1$-$C_4$ alkylcarboxy, unsubstituted $C_1$-$C_4$ alkylamide, unsubstituted $C_1$-$C_4$ alkylester, or a moiety of Formula (II); each R³ and R⁴ in Formulas (I) and (II) is independently hydroxy, unsubstituted $C_1$-$C_4$ alkyl, or unsubstituted $C_1$-$C_4$ alkoxy; and/or each A in Formulas (I) and (II) is independently $C_1$-$C_4$ alkylene.

In other embodiments, R¹ and R² are each independently hydrogen, unsubstituted $C_1$-$C_4$ alkyl, or a moiety of Formula (II); each R³ and R⁴ in Formulas (I) and (II) is independently hydroxy, unsubstituted $C_1$-$C_4$ alkoxy; and/or each A in Formulas (I) and (II) is independently methylene or ethylene. In further embodiments, at least one of R¹ and R² is a moiety of Formula (II).

In certain embodiments, the compound of Formula (I) is:

Further, in accordance with the present invention, metal-binding bifunctional compounds include compounds of Formula (III) or a pharmaceutically acceptable salt thereof:

wherein each R⁵ is independently hydrogen, hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

R⁶ is hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester, or a moiety of Formula (IV):

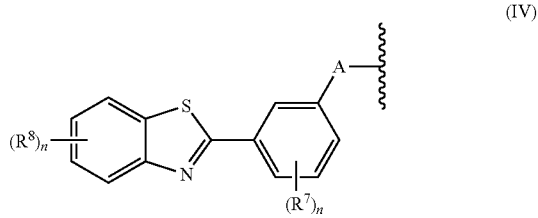

each R⁷ and R⁸ of Formulas (III) and (IV) are independently hydroxy, halo, nitro, amino, substituted or unsubstituted $C_1$-$C_4$ alkyl, substituted or unsubstituted $C_1$-$C_4$ alkoxy, substituted or unsubstituted aryl, or unsubstituted or substituted heteroaryl;

each n is independently 0 to 4, 0 to 3, 0 to 2, 1, or 0; and each A in Formulas (III) and (IV) is independently $C_1$-$C_4$ alkylene, carbonyl, amide, thioamide, sulfonamide, urea, or carbamate.

In various embodiments, each $R^5$ is independently hydrogen, hydroxy, halo, unsubstituted $C_1$-$C_4$ alkyl, or unsubstituted $C_1$-$C_4$ alkoxy; $R^6$ is hydrogen, unsubstituted $C_1$-$C_4$ alkyl, unsubstituted $C_1$-$C_4$ alkylcarboxy, unsubstituted $C_1$-$C_4$ alkylamide, unsubstituted $C_1$-$C_4$ alkylester, or a moiety of Formula (IV); each $R^7$ and $R^8$ of Formulas (III) and (IV) are independently hydroxy, unsubstituted $C_1$-$C_4$ alkyl, or unsubstituted $C_1$-$C_4$ alkoxy; and/or each A in Formulas (III) and (IV) is independently $C_1$-$C_4$ alkylene.

In various embodiments, each $R^5$ is independently hydrogen, halo, or unsubstituted $C_1$-$C_4$ alkoxy; $R^6$ is hydrogen, unsubstituted $C_1$-$C_4$ alkyl, unsubstituted $C_1$-$C_4$ alkylcarboxy, unsubstituted $C_1$-$C_4$ alkylester, or a moiety of Formula (IV); each $R^7$ and $R^8$ of Formulas (III) and (IV) is independently hydroxy, or unsubstituted $C_1$-$C_4$ alkoxy; and/or each A in Formulas (III) and (IV) is independently is methylene or ethylene. In further embodiments, $R^6$ is a moiety of Formula (IV).

In various embodiments, the compound of Formula (III) is selected from the group consisting of:

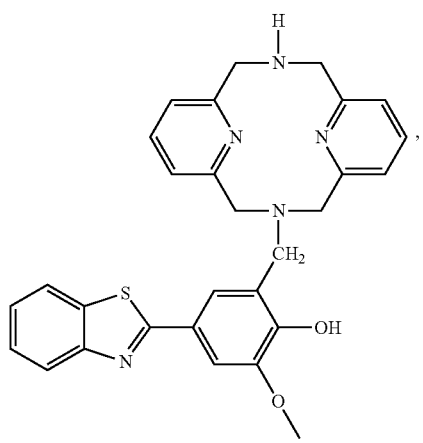

,

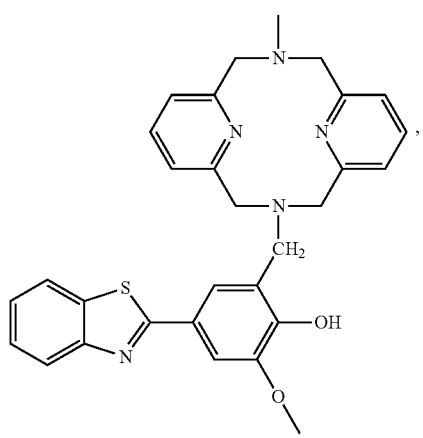

,

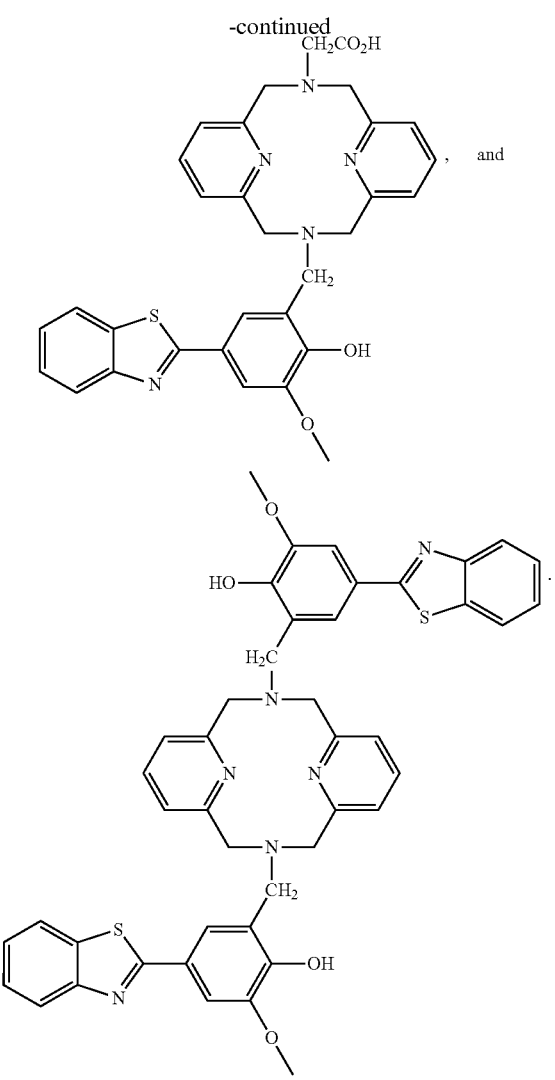

, and

.

Also, in accordance with the present invention, metal-binding bifunctional compounds include compounds of Formula (V) or a pharmaceutically acceptable salt thereof:

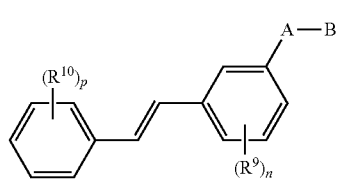

(V)

wherein
B is a moiety selected from the group consisting of:

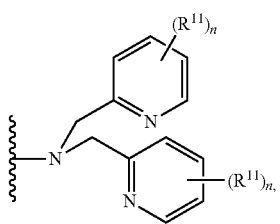

,

-continued

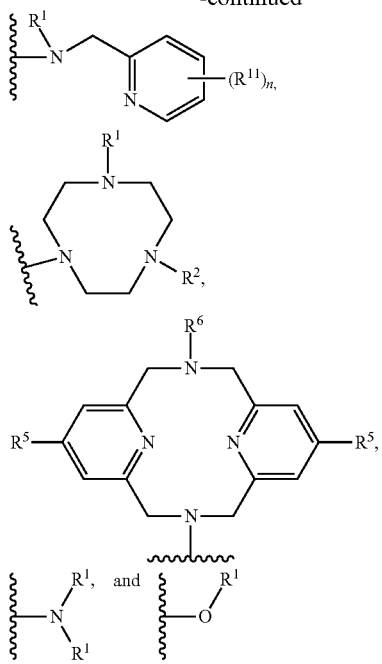

each $R^1$ and $R^2$ is independently hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester;

each $R^5$ is independently hydrogen, hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

$R^6$ is hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester, or a moiety of Formula (VI):

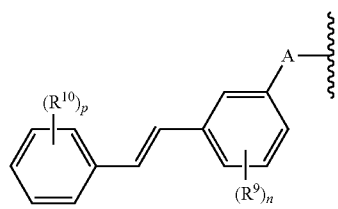

(VI)

each A in Formulas (V) and (VI) is independently $C_1$-$C_4$ alkylene, carbonyl, amide, thioamide, sulfonamide, urea, or carbamate;

each $R^9$ and $R^{16}$ in Formulas (V) and (VI) is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

each $R^{11}$ is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;

each n is independently 0 to 4, 0 to 3, 0 to 2, 1, or 0; and
each p in Formulas (V) and (VI) is independently 0 to 5, 0 to 4, 0 to 3, 0 to 2, 1, or 0.

In various embodiments, as it relates to Formulas (V) and (VI), each $R^1$ and $R^2$ is independently hydrogen, unsubstituted $C_1$-$C_4$ alkyl, unsubstituted aryl, unsubstituted heteroaryl, unsubstituted $C_1$-$C_4$ alkylcarboxy, unsubstituted $C_1$-$C_4$ alkylamide, or unsubstituted $C_1$-$C_4$ alkylester; each $R^5$ is independently hydrogen, hydroxy, halo, unsubstituted $C_1$-$C_4$ alkyl, or unsubstituted $C_1$-$C_4$ alkoxy; $R^6$ is hydrogen, unsubstituted $C_1$-$C_4$ alkyl, unsubstituted $C_1$-$C_4$ alkylcarboxy, unsubstituted $C_1$-$C_4$ alkylamide, unsubstituted $C_1$-$C_4$ alkylester, or a moiety of Formula (VI); each A in Formulas (V) and (VI) is independently $C_1$-$C_4$ alkylene; each $R^9$ and $R^{16}$ in Formulas (V) and (VI) are independently hydroxy, unsubstituted $C_1$-$C_4$ alkyl, or unsubstituted $C_1$-$C_4$ alkoxy; and/or each $R^{11}$ is independently hydroxy, halo, unsubstituted $C_1$-$C_4$ alkyl, or unsubstituted $C_1$-$C_4$ alkoxy.

In other embodiments, as it relates to Formulas (V) and (VI), each $R^1$ and $R^2$ is independently hydrogen or unsubstituted $C_1$-$C_4$ alkyl; each $R^5$ is independently hydrogen, halo, or unsubstituted $C_1$-$C_4$ alkoxy; $R^6$ is hydrogen, unsubstituted $C_1$-$C_4$ alkyl, unsubstituted $C_1$-$C_4$ alkylcarboxy, unsubstituted $C_1$-$C_4$ alkylester, or a moiety of Formula (VI); each A in Formulas (V) and (VI) is independently methylene or ethylene; each $R^9$ and $R^{16}$ in Formulas (V) and (VI) are independently hydroxy, or unsubstituted $C_1$-$C_4$ alkoxy; and/or each $R^{11}$ is independently halo, or unsubstituted $C_1$-$C_4$ alkoxy.

In some embodiments, the compound of Formula (V) is a compound of Formula (VII):

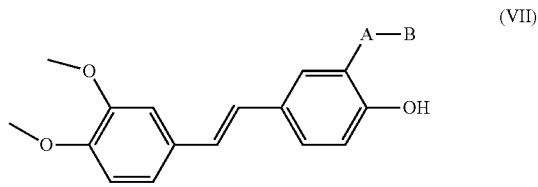

(VII)

wherein A and B are defined above with respect to Formulas (V) and (VI).

In certain embodiments, the compound of Formula (V) is selected from the group consisting of:

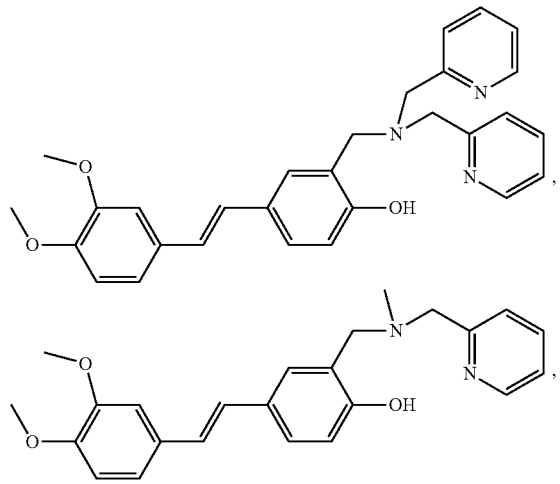

17
-continued

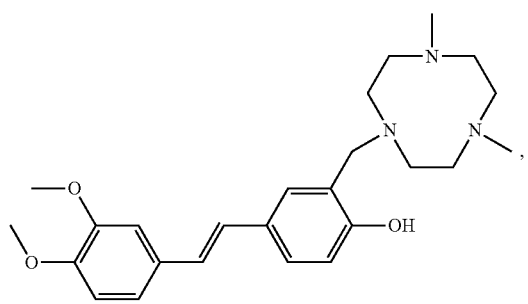

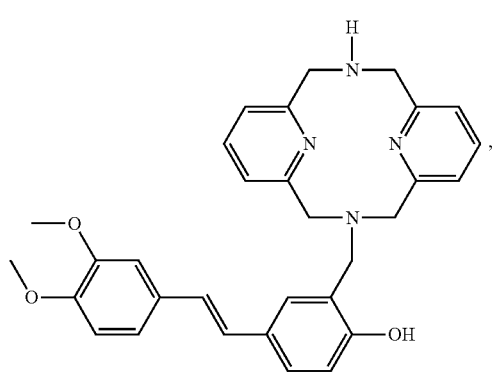

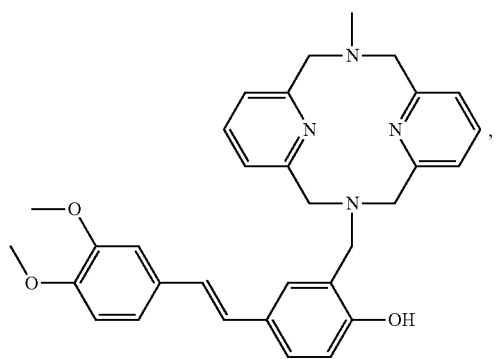

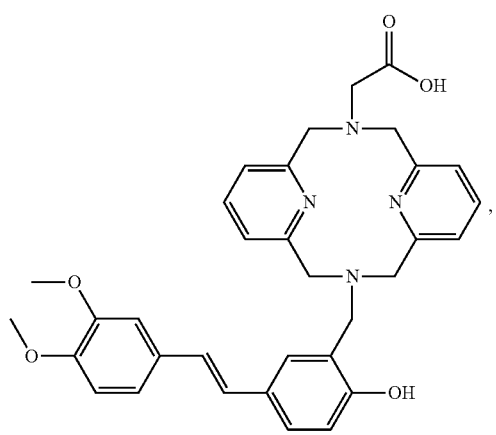

18
-continued

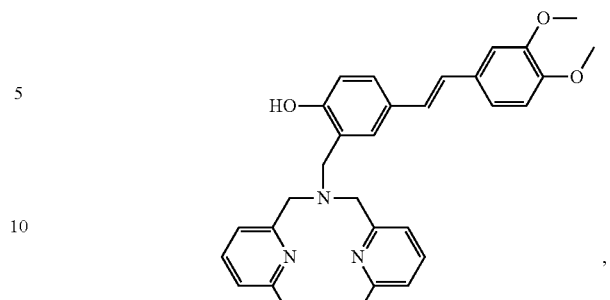

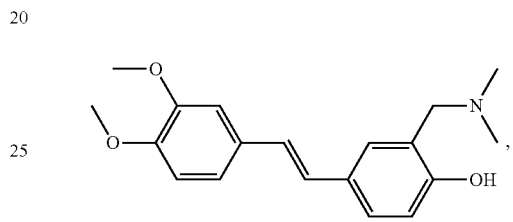

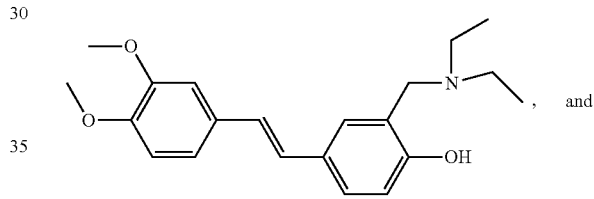

A further aspect of the present invention is directed to metal radionuclide complexes comprising any one of compounds of Formulas (I), (III), and (V) and a metal radionuclide, for example with an isotope useful for positron emission tomography. Because PET works by detecting 511 keV gamma rays that are produced by the annihilation of positrons (β+) emitted by a radionuclide and nearby electrons, an ideal PET radionuclide should have a low β+ energy and high β+ branching ratio. Further, the physical half-life of a radionuclide should match the biological half-life of the molecule to be labeled. Metal radionuclides suitable for use in the present invention include, but are not limited to Tc-99m(=O), Ga-66, Y-86, Zr-89, Co-55, Mn-52, Cu-60, Cu-61, Cu-62, or Cu-64. Preferably, the metal radionuclide is selected from the group consisting of Cu-60, Cu-61, Cu-62, and Cu-64. More preferably, the metal radionuclide comprises copper-64 (Cu-64).

Examples radiolabeled compounds of the present invention include compounds of Formulas (VIII)-(XI) or salts thereof:

(VIII)

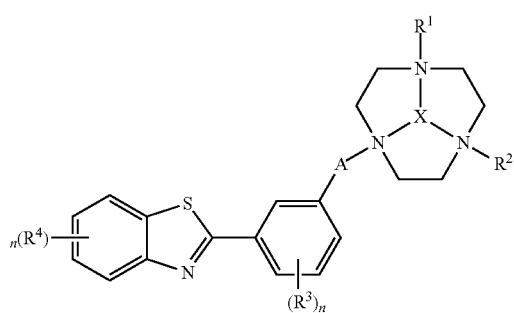

(IX)

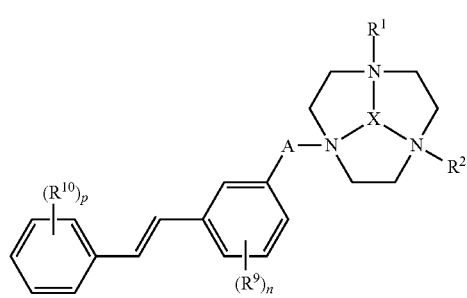

(X)

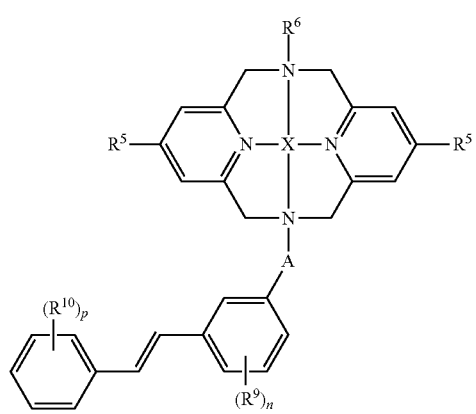

(XI)

wherein X is a radionuclide of Co, Cu, Ga, Mn, Tc=O, Y, or Zr. In some embodiments, the metal radionuclide is selected from the group consisting of Cu-60, Cu-61, Cu-62, and Cu-64.

Bifunctional compound L3 can be synthesized through a Mannich reaction of 2-(4-hydroxy-3-methoxy)benzothiazole with paraformaldehyde and 1,4-dimethyl-1,4,7-triazacyclononane (Scheme 1).

Scheme 1: Synthesis of Compound L3

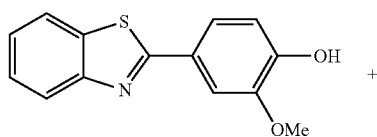

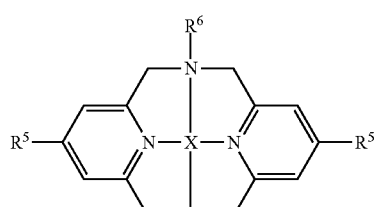

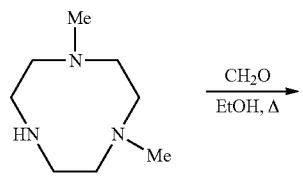

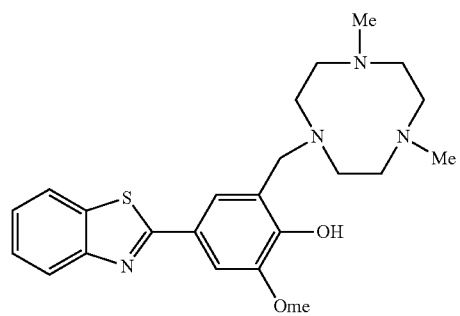

Mannich reaction of 2-(4-hydroxy-3-methoxy)benzothiazole with paraformaldehyde and 2,11-diaza[3.3](2,6)pyridinophane yielded bifunctional compound L4 with a tetraazamacrocyclic binding fragment (Scheme 2, R=H). Similarly, Mannich reaction with the N-methyl derivative of 2,11-diaza[3.3](2,6)pyridinophane gave the corresponding compound L5 (R=Me). Reaction of compound L4 with tert-butylbromoacetate and subsequent acid hydrolysis of the ester yielded compound L6 (R=CH$_2$CO$_2$H). Finally, a double Mannich reaction between 2-(4-hydroxy-3-methoxy)benzothiazole and 2,11-diaza[3.3](2,6)pyridinophane yielded compound L7.

Scheme 2: Synthesis of Compounds L4-L7

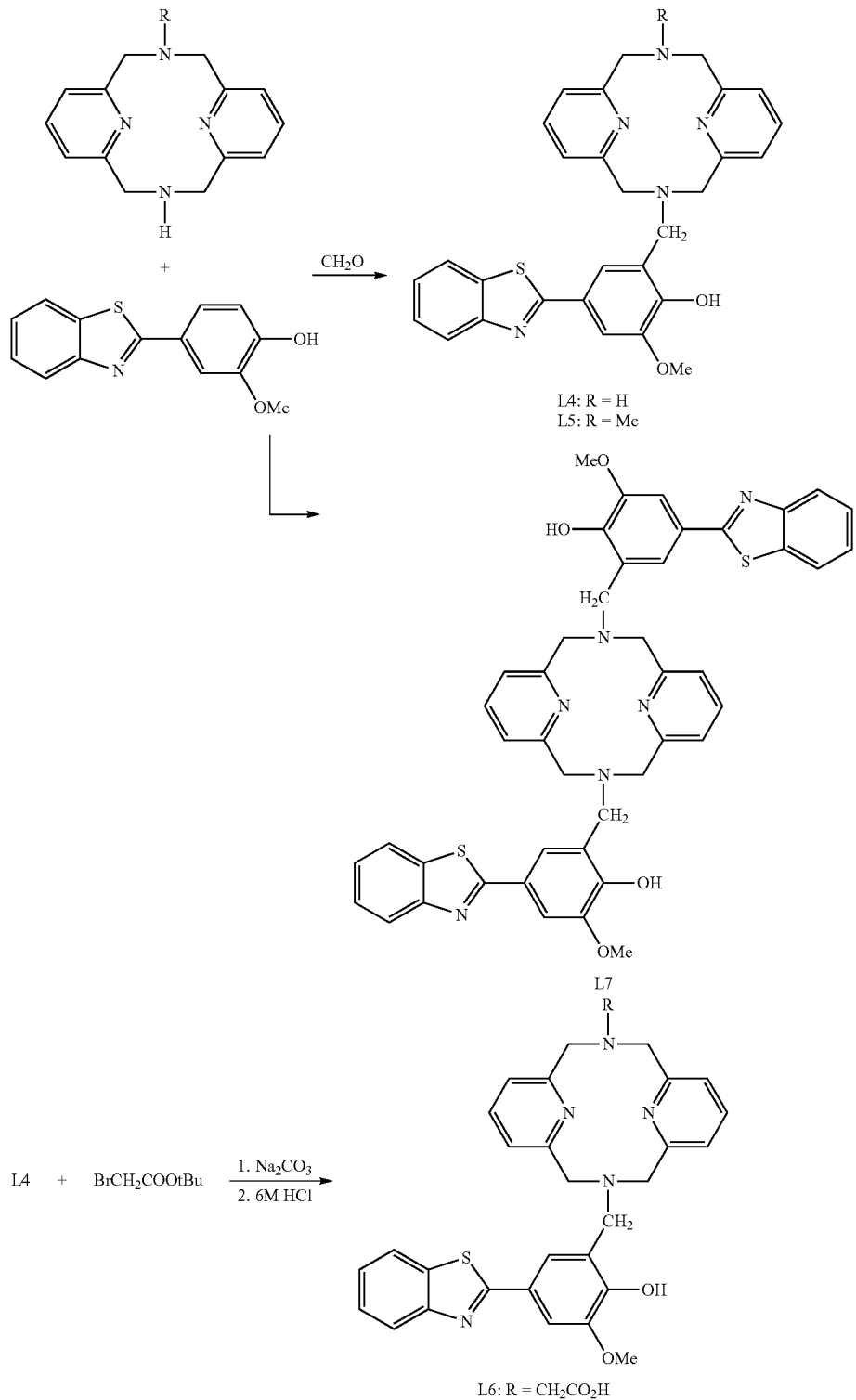

In other aspects, the present invention is directed to a method for diagnosing or monitoring a β-amyloid disease in a subject comprising administering a radiopharmaceutical composition comprising a radionuclide complex of Formula (I) or Formula (III) to the subject; imaging the subject's brain by position emission tomography; and detecting the binding of the metal radionuclide complex to Aβ species.

The methods of the present invention can be practiced on patients with diseases characterized by amyloid deposits including Aβ in the brain, or patients at risk of such a disease.

Such diseases include Alzheimer's disease, dementia with Lewy bodies (DLB), cerebral amyloid angiopathy (CAA), Down's syndrome, mild cognitive impairment, and posterior cortical atrophy (PCA).

When labeled with a radioisotope such as copper-64, the metal complexes can be used as positron emission tomography (PET) ligands to detect Aβ species in the brain. The in vivo detection of Aβ species, such as β-amyloid plaques and neurofibrillary tangles (NFTs), is useful for not only for the early diagnosis of Alzheimer's disease, but also to monitor disease progression.

An effective diagnostic marker enables accurate enrollment of early stage AD patients into trials of therapeutic interventions targeting disease progression. If progressive accumulation of Aβ within individual regions or across multiple brain regions correlates with disease progression, particularly in early and intermediate disease stages, an Aβ imaging agent could improve evaluation of therapeutic efficacy for candidate disease-modifying interventions.

One diagnostic method that is suitable for use with the bifunctional compounds of the present invention is positron emission tomography (PET). PET is known in the art of nuclear medicine imaging as a non-invasive imaging modality that can provide functional information of a living subject at the molecular and cellular level. PET utilizes biologically active molecules in micromolar or nanomolar concentrations that have been labeled with short-lived positron emitting isotopes. The physical characteristics of the isotopes and the molecular specificity of labeled molecules, combined with the high detection efficacy of modern PET scanners provides a sensitivity for in vivo measurements of indicator concentrations that is several orders of magnitude higher than with other imaging techniques.

In order to make measurements with PET, a biologically active tracer molecule tagged with a positron-emitting isotope is administered to a subject, for example, intravenously, orally, or by inhalation. The subject is then scanned, and axial tomographic slices of regional cerebral tracer accumulation are obtained. This tracer accumulation can be related to cerebral metabolism, blood flow, or binding site concentrations by appropriate mathematical models. Thus, by using a small molecular PET radiotracer which has high affinity and selectivity for Aβ aggregates, the level of Aβ aggregation can be quantified. This approach not only improves the diagnostic accuracy of AD, but also provides a tool to monitor the progression of the disease and the efficacy of the treatment, and improve the understanding of disease progression.

Certain metal radionuclide complexes of the bifunctional compounds of the present invention are suitable for use as PET ligands. The PET ligands for use in the present methods bind to Aβ or other component of amyloid deposits found in Alzheimer's and related diseases characterized by deposits of Aβ in the brain. Amyloid deposits (also known as plaques) are aggregates of Aβ present in the brain of AD patients and are substantially insoluble in aqueous solution, such as body fluids. Amyloid deposits can also be formed by in vitro aggregation of Aβ to an insoluble mass.

The affinity of binding to a deposit may depend on whether the deposit is formed in vitro, in a transgenic animal, or in a human. The PET ligands of the invention preferentially bind to Aβ in the form of amyloid deposits with an affinity in the range of 20-600 nM. Binding to amyloid deposits in the brain serves to immobilize a PET ligand to an insoluble structure in the brain and allows development of an image. Some PET ligands preferentially bind to fibrillar amyloid over other forms of amyloid deposits.

PET ligands are preferably small molecules, meaning they have a molecular weight less than 1000 Da and preferably less than 500 Da. PET ligands are preferably able to cross the blood brain barrier to allow peripheral administration.

The PET ligands of the present invention may be administered to a human subject as a pharmaceutically acceptable salt. Such salts and common methodology for preparing them are well known in the art. (See, for example, Stahl, P. H., and Wermuth, C. G. (Eds.), 2002, *Pharmaceutical salts: Properties, Selection, and Use*, Wiley-VCH). Pharmaceutically acceptable acid salts include hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate [i.e., 1,1'-methylene-bis-(2-hydroxy-3-naphthoate)] salts. Suitable base salts include aluminum, calcium, lithium, magnesium, potassium, sodium, zinc, and diethanolamine salts.

The dose of PET ligand administered can be measured by radioactivity. An exemplary dose for the PET ligands of the present invention is 10 µCi to 10 mCi.

In a yet further aspect, the present invention provides a radiopharmaceutical composition comprising the PET ligand as defined herein together with a biocompatible carrier suitable for mammalian administration. The "biocompatible carrier" is a fluid, especially a liquid, in which the PET ligand of the invention is suspended or dissolved, such that the radiopharmaceutical composition can be administered to the mammalian body without toxicity or undue discomfort. The biocompatible carrier is suitably an injectable carrier liquid such as sterile water for injection; an aqueous solution such as saline; an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethylene glycols, propylene glycols and the like). The biocompatible carrier may also comprise biocompatible organic solvents such as ethanol. Such organic solvents are useful to solubilize more lipophilic compounds or formulations. Preferably the biocompatible carrier is sterile water for injection, isotonic saline, or an aqueous ethanol solution. The pH of the biocompatible carrier for intravenous injection is suitably in the range 4.0 to 10.5.

The radiopharmaceutical composition may be administered parenterally, i.e. by injection, and is most preferably an aqueous solution. Such a composition may optionally contain further ingredients such as buffers, pharmaceutically acceptable solubilizers, pharmaceutically acceptable stabilizers, or antioxidants. Where the PET ligand of the invention is provided as a radiopharmaceutical, the method for preparation of said PET ligand may further comprise the steps required to obtain a radiopharmaceutical composition (e.g. removal of organic solvent, addition of a biocompatible buffer, and any optional further ingredients). For parenteral administration, steps to ensure that the radiopharmaceutical composition is sterile, apyrogenic, free from extraneous particles and of suitable pH need to be taken. Such steps are well-known to those of skill in the art.

The amount of administered radiopharmaceutical to be used for the Aβ species imaging will depend on the age, sex, weight, and condition of the patient. This can be adjusted as required by a skilled physician. It will be appreciated by those in the art that the quantity of the labelled probe required for diagnostic imaging will be relatively small. Dosages can range from 0.001 mg/kg to 1000 mg/kg, however smaller quantities in the range of 0.1 mg/kg to 100 mg/kg are preferred.

As used herein, the terms "amyloid peptide" "amyloid β peptide" and "Aβ" are used interchangeably to refer to the family of peptides generated through proteolytic processing of amyloid precursor protein (APP).

As used herein, Aβ species may comprise amyloid polypeptides of various length, various aggregation states, and/or solubility.

In general the aggregation status of Aβ peptides may be broken into three categories: (1) micelles; (2) protofibrils; and (3) fibrils. The aggregation state of beta amyloid species may be determined using the techniques set out in Goldsbury et. al, J. Struct. Biol., June; 130(2-3): 352-62, (2000), in which samples are classified by the amount of β strands in undisturbed solution (pH 7.4 at 37° C.) by circular dichroism. Under these conditions (1) micelles demonstrate 0% β strands; (2) protofibrils demonstrate about 76% β strands; and (3) fibrils demonstrate 100% β strands.

As used herein, the terms "fibrils" and "fibrillar" generally refer to Aβ species with largely beta-sheet content that are insoluble aggregates. Fibrils bind Congo Red and Thioflavin T dyes and cause these dyes to produce fluorescence signal. Fibril preparations preferentially comprise substantially fibrillar Aβ, but they may also comprise unsubstantial amounts of globular aggregates.

EXAMPLES

The following non-limiting examples are provided to further illustrate the present invention.

Example 1

Synthesis of L3

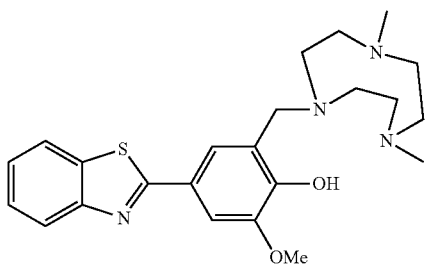 [SMILES: COc1cc(-c2nc3ccccc3s2)cc(CN2CCN(C)CCN(C)CC2)c1O]

Paraformaldehyde (0.204 g, 6.68 mmol) was added to a solution of 1,4-dimethyl-1,4,7-triazacyclononane (0.7 g, 4.45 mmol) in acetonitrile (5 mL) and the resulting mixture was heated to reflux for 30 minutes. Then 2-(4-hydroxy-3-methoxy)-benzothiazole (1.145 g, 4.45 mmol) in acetonitrile (35 mL) was added and the solution was refluxed for 24 hours under nitrogen. Upon cooling to room temperature, the solvent was removed to give a reddish residue that was purified by silica gel column chromatography using $CHCl_3$:MeOH:$NH_4OH$ (90:5:5 ratio) to yield L3 as a yellow oil which turned into solid when stored at −20° C. (0.55 g, Yield 30%). $^1$H NMR (CDCl$_3$): δ 8.01 (d, 1H, ArH), 7.86 (d, 1H, ArH), 7.54 (s, 1H, ArH), 7.45 (t, 1H, ArH), 7.35-7.31 (m, 2H, ArH), 4.10 (s, 3H, OCH$_3$), 3.93 (s, 2H, NCH$_2$Py), 3.01 (t, 4H, CH$_2$N), 2.72 (t, 4H, CH$_2$N), 2.56 (s, 4H, CH$_2$N), 2.39 (s, 6H, NCH$_3$). $^{13}$C NMR (300 MHz, CDCl$_3$)/δ (ppm): 168.52, 154.19, 151.58, 148.52, 134.70, 126.12, 124.57, 123.81, 122.92, 122.56, 121.42, 120.62, 109.61, 60.52, 58.55, 57.99, 56.11, 53.14, 46.72. UV-vis (MeCN, $\lambda_{max}$, nm, (ε, M$^{-1}$ cm$^{-1}$) 330 (18 200). ESI-MS: Calcd for [M+H]$^+$, 427.1. found, 427.1.

Example 2

Synthesis of L4

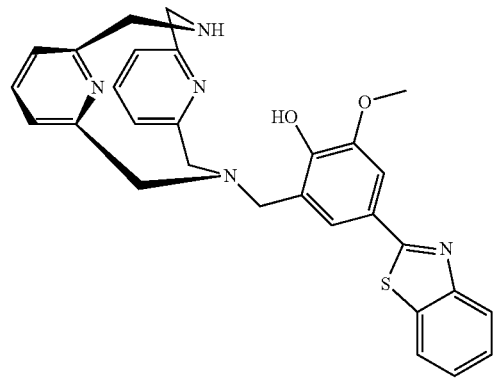

Paraformaldehyde (0.0062 g, 0.208 mmol) was added to a solution of 2,11-diaza[3.3](2,6)pyridinophane ("N$_4$H$_2$") (0.050 g, 0.208 mmol) in acetonitrile (2 mL) and the resulting mixture was heated to reflux for 1 hour. A solution of 2-(4-hydroxy-3-methoxy)benzothiazole (0.054 g, 0.208 mmol) in acetonitrile (5 mL) was added to the reaction flask and the solution was refluxed for another 24 hours under nitrogen. The solvent was removed and the resulting residue was purified by silica gel column chromatography. Ethyl acetate was used to elute starting material 2-(4-hydroxy-3-methoxy)benzothiazole, CHCl$_3$:MeOH (90:10 ratio) was used to elute dibenzothiazolated compound (L7), and CHCl$_3$:MeOH (80:20 ratio) was used to elute L4. The solvent was removed to yield L4 as a yellow compound (0.062 g, Yield 60%). $^1$H NMR (CDCl$_3$): δ 8.03 (d, 1H, ArH), 7.88 (d, 1H, ArH), 7.64 (s, 1H, ArH), 7.53 (s, 1H, ArH), 7.45 (t, 1H, ArH), 7.35 (t, 1H, ArH), 7.12 (t, 2H, PyH), 6.73 (d, 2H, PyH), 6.54 (d, 2H, PyH), 4.29 (s, 2H, NCH$_2$—), 4.07 (s, 4H, CH$_2$NCH$_2$), 4.06 (s, 3H, OCH$_3$), 4.07 (s, 4H, CH$_2$NHCH$_2$). $^{13}$C NMR (300 MHz, CDCl$_3$)/δ (ppm): 168.17, 156.52, 154.12, 136.51, 134.77, 126.24, 123.24, 122.69, 121.88, 121.53, 120.97, 110.70, 63.33, 56.37, 55.09. UV-vis (MeCN, $\lambda_{max}$, nm, (ε, M$^{-1}$ cm$^{-1}$) 334 (15 800). ESI-MS: Calcd for [M+H]$^+$, 510.1964. Found, 510.2.

Example 3

Synthesis of L5

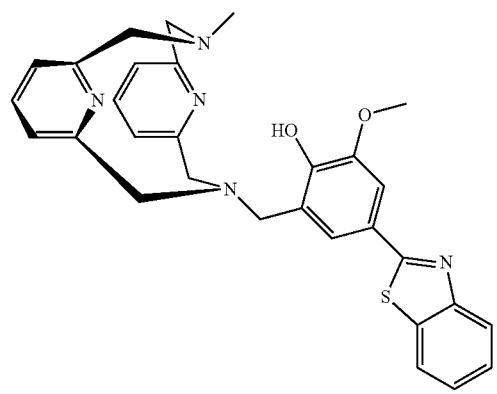

Paraformaldehyde (0.0088 g, 0.295 mmol) was added to a solution of the monomethyl derivative of 2,11-diaza[3.3](2,6)pyridinophane ("N₄MeH")(0.050 g, 0.196 mmol) in acetonitrile (5 mL) and the resulting mixture was heated to reflux for 1 hour. A solution of 2-(4-hydroxy-3-methoxy)benzothiazole (0.076 g, 0.295 mmol) in acetonitrile (5 mL) was added to the reaction flask and the solution was refluxed for another 24 hours under nitrogen. The solvent was removed and the resulting residue was purified by silica gel column chromatography. Ethyl acetate was used to elute starting material 2-(4-hydroxy-3-methoxy)benzothiazole and then CHCl₃:MeOH:NH₄OH (80:15:5 ratio) was used to elute L5. The solvent was removed to yield L5 as a yellow compound (0.045 g, Yield 44%). $^1$H NMR (CDCl₃): δ 8.02 (d, 1H, ArH), 7.86 (d, 1H, ArH), 7.63 (s, 1H, ArH), 7.48 (s, 1H, ArH), 7.45 (t, 1H, ArH), 7.33 (t, 1H, ArH), 7.14 (t, 2H, PyH), 6.80 (t, 4H, PyH), 4.24 (s, 2H, NCH₂—), 4.08 (s, 4H, CH₂NCH₂), 4.05 (s, 3H, OCH₃), 3.82 (s, 4H, CH₂NHCH₂), 2.71 (s, 3H, NCH₃). $^{13}$C NMR (300 MHz, CDCl₃)/δ (ppm): 168.05, 154.11, 150.09, 148.74, 126.25, 125.06, 124.81, 123.066, 122.71, 122.61, 121.51, 120.76, 110.165, 65.91, 59.81, 56.22, 42.73. UV-vis (MeCN, $\lambda_{max}$, nm, (ε, M⁻¹ cm⁻¹) 330 (9740). ESI-MS: Calcd for [M+H]⁺, 524.2. Found, 524.2.

Example 4

Synthesis of L6

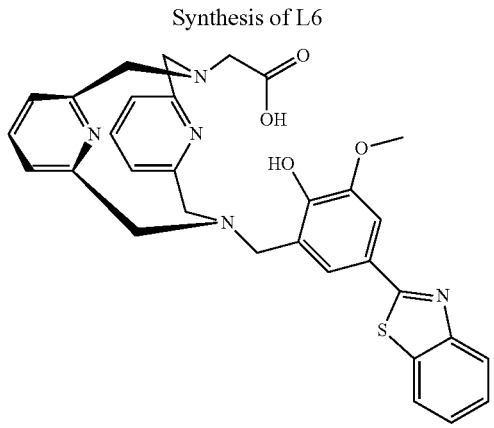

To a solution of L4 (0.045 g, 0.088 mmol) in acetonitrile (5 mL) was added sodium carbonate (0.0093 g, 0.088 mmol) followed by addition of tert-butyl bromoacetate (0.0172 g, 0.088 mmol). The resulting mixture was stirred for 3 hours at room temperature under nitrogen. The solvent was removed and the resulting residue was purified by silica gel column chromatography using CHCl₃:MeOH (95:5 ratio). The solvent was removed to yield the t-butyl ester of L6 as a yellow solid (0.054 g, Yield 98%). [Characterization: $^1$H NMR (CDCl₃): δ 7.96 (d, 1H, ArH), 7.88 (d, 1H, ArH), 7.58-7.34 (m, 4H, ArH), 7.08 (t, 2H, ArH), 6.54-6.47 (m, 2H, ArH), 4.39-4.21 (m, 8H, NCH₂—), 4.07 (s, 3H, OCH₃), 3.97-3.90 (s, 2H, CH₂NCH₂), 3.58 (s, 2H, CH₂NHCH₂), 1.49 (s, 9H, tBu). HRMS: Calcd for [M+H]⁺, 624.2645. Found, 624.3).

This yellow solid was dissolved in 6M HCl and then stirred for 12 h at room temperature. Solvent was removed under vacuum to yield L6 as a yellow solid. $^1$H NMR (CD₃OD): δ 8.24 (s, 1H, ArH), 8.11-8.03 (m, 2H, ArH), 7.89 (s, 1H, ArH), 7.67-7.51 (m, 4H, ArH), 7.20-7.12 (m, 4H, ArH), 5.07 (s, 2H, NCH₂), 4.90 (m, 8H, NCH2), 4.71 (s, 2H, NCH₂), 4.09 (s, 3H, OCH₃). $^{13}$C NMR (300 MHz, CD₃OD)/δ (ppm): 190.57, 166.98, 154.24, 149.71, 149.43, 148.93, 138.81, 132.43, 131.15, 128.54, 127.01, 126.44, 123.57, 123.44, 119.69, 118.57, 111.56, 60.68, 59.47, 56.07, 55.80, 53.16. UV-vis (MeCN, $\lambda_{max}$, nm, (ε, M⁻¹ cm⁻¹) 331 (12 300). ESI-MS: Calcd for [M+H]⁺, 568.2019. Found, 568.2.

Example 5

Synthesis of L7

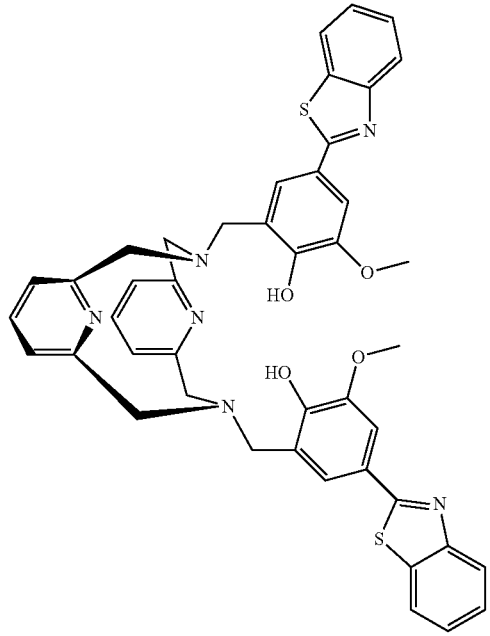

The synthesis and purification of L7 was described previously in Example 2. Yield 16%. $^1$H NMR (CDCl₃): δ 7.99 (d, 1H, ArH), 7.84 (d, 1H, ArH), 7.64 (s, 1H, ArH), 7.47 (s, 1H, ArH), 7.45 (t, 1H, ArH), 7.33 (t, 1H, ArH), 7.18 (t, 2H, PyH), 6.83 (d, 2H, PyH), 4.23 (s, 4H, NCH₂—), 4.05 (s, br, 6H, —OCH₃ and 8H, CH₂NCH₂). $^{13}$C NMR (300 MHz, CDCl₃)/δ (ppm): 168.04, 155.75, 154.10, 150.06, 148.79, 134.76, 126.26, 125.10, 124.82, 123.06, 122.71, 120.74, 110.24, 63.67, 56.24. UV-vis (MeCN, $\lambda_{max}$, nm, (ε, M⁻¹ cm⁻¹) 323 (19 600). ESI-MS: Calcd for [M+H]⁺, 779.2474. Found, 779.3.

Example 6A-6E

Synthesis of the Copper Complexes of L3-L7

Example 6A

Synthesis of (L3)Cu$^{II}$Cl

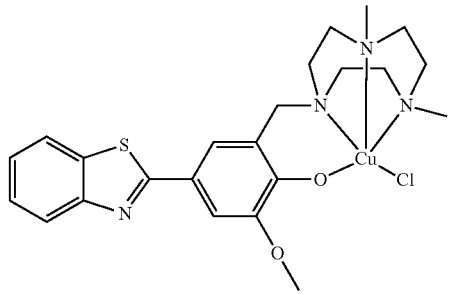

To a stirred solution of L3 (0.125 g, 0.293 mmol) in acetonitrile (5 mL) and triethylamine (0.044 g, 0.44 mmol) was added a solution of cupric chloride (CuCl$_2$) (0.040 g, 0.293 mmol) in acetonitrile (2 mL). The brown colored solution was stirred for 30 minutes. Addition of diethyl ether resulted in the formation of a brown precipitate which was filtered, washed with diethyl ether, and dried under vacuum (0.085 g, Yield 55%). UV-vis (MeCN, $\lambda_{max}$, nm, ($\epsilon$, M$^{-1}$cm$^{-1}$)) 353 (7500), 425 (sh, 450), 515 (sh, 250), 650 (90). ESI-MS: Calcd for [(L1)Cu]$^+$, 488.1307. Found, 488.1. Anal. Found: C, 48.42; H, 6.69; N, 9.47. Calcd for C$_{23}$H$_{29}$ClN$_4$O$_2$SCu.2.5H$_2$O: C, 48.50; H, 6.02; N, 9.84.

Example 6B

Synthesis of [(L4)Cu$^{II}$]$_2$(ClO$_4$)$_2$

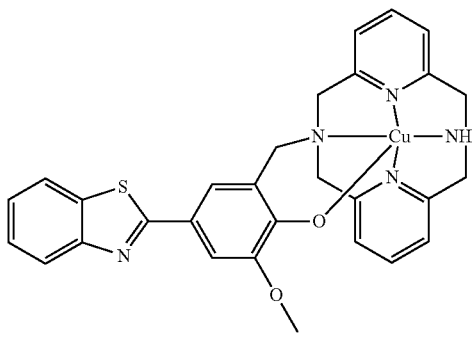

A solution of [Cu$^{II}$(H$_2$O)$_6$](ClO$_4$)$_2$ (0.036 g, 0.098 mmol) was added to a stirred solution of L4 (0.050 g, 0.098 mmol) in methanol (5 mL) and triethylamine (0.015 g, 0.147 mmol). The brown colored solution was stirred for 12 hours. A reddish brown precipitate was formed which was filtered, washed with diethyl ether, and dried under vacuum (0.052 g, Yield 79%). UV-vis (MeCN, $\lambda_{max}$, nm, ($\epsilon$, M$^{-1}$cm$^{-1}$)) 363 (15 000), 428 (1500), 505 (450), 725 (130). ESI-MS: Calcd for [(L2)Cu]$^+$, 571.1. Found, 571.1. Anal. Found: C, 51.15; H, 3.86; N, 10.20. Calcd for C$_{58}$H$_{52}$Cl$_2$N$_{10}$O$_4$S$_2$Cu$_2$: C, 51.86; H, 3.90; N, 10.43.

Example 6C

Synthesis of [(L5)Cu$^{II}$](ClO$_4$)

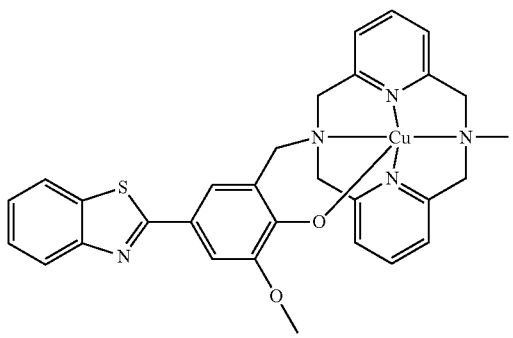

A solution of [Cu$^{II}$(H$_2$O)$_6$](ClO$_4$)$_2$ (0.042 g, 0.114 mmol) was added to a stirred solution of L5 (0.060 g, 0.114 mmol) in methanol (5 mL) and triethylamine (0.018 g, 0.171 mmol). The brown colored solution was stirred for 12 hours. Addition of diethyl ether (30 mL) resulted in the formation of brown precipitate which was filtered, washed with diethyl ether, and dried under vacuum (0.052 g, Yield 79%). UV-vis (MeCN, $\lambda_{max}$, nm, ($\epsilon$, M$^{-1}$ cm$^{-1}$)) 357 (14 700), 421 (1600), 520 (430), 710 (150). ESI-MS: Calcd for [(L3)Cu]$^+$, 585.1. Found, 585.1. Anal. Found: C, 48.43; H, 4.10; N, 9.38. Calcd for C$_{30}$H$_{34}$ClN$_5$O$_9$SCu.3H$_2$O: C, 48.71; H, 4.63; N, 9.47.

Example 6D

Synthesis of [(L6)Cu$^{II}$]

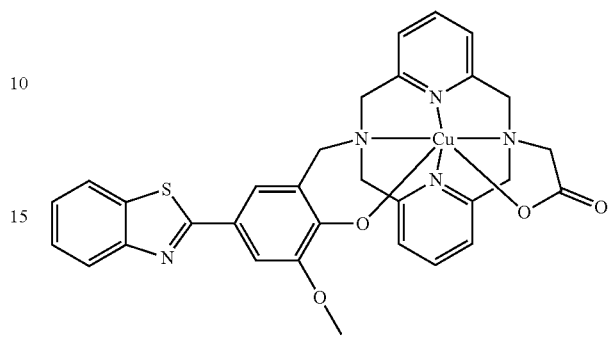

A solution of [Cu$^{II}$(H$_2$O)$_6$](ClO$_4$)$_2$ (0.032 g, 0.088 mmol) was added to a stirred solution of L6 (0.050 g, 0.088 mmol) in methanol (5 mL), which formed a green colored solution. Dropwise addition of triethylamine (0.045 g, 0.44 mmol) resulted in a deep brown colored solution which was stirred for 12 hours. Addition of diethyl ether (20 mL) resulted in the formation of brown precipitate which was filtered, washed with diethyl ether, and dried under vacuum (0.042 g, Yield 65%). UV-vis (MeCN, $\lambda_{max}$, nm, ($\epsilon$, M$^{-1}$cm$^{-1}$)) 358 (12 000), 425 (1300), 500 (430), 761 (120). ESI-MS: Calcd for [(L4)Cu]$^+$, 629.1. Found, 629.1. Anal. Found: C, 46.12; H, 4.22; N, 8.63. Calcd for C$_{32}$H$_{31}$ClN$_5$O$_8$SCu.4.3H$_2$O: C, 46.19; H, 4.45; N, 8.69.

Example 6E

Synthesis of [(L7)Cu$^{II}$]

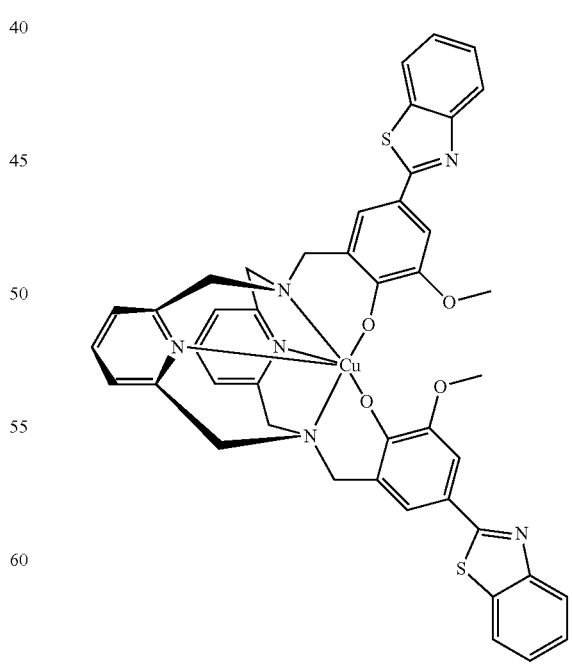

A solution of [Cu$^{II}$(H$_2$O)$_6$](ClO$_4$)$_2$ (0.056 g, 0.088 mmol) was added to a stirred solution of L7 (0.118 g, 0.151 mmol) in methanol (5 mL). The deep brown solution was stirred for 12 hours. Addition of diethyl ether (30 mL) resulted in the formation of a brown precipitate which was filtered, washed with diethyl ether, and dried under vacuum (0.101 g, Yield 79%). UV-vis (MeCN, $\lambda_{max}$, nm, ($\epsilon$, $M^{-1}cm^{-1}$)) 324 (14 000), 410 (4500), 560 (1400), 750 (sh, 180). ESI-MS: Calcd for [(L5)Cu]$^+$, 840.1614. Found, 840.2. Anal. Found: C, 51.04; H, 3.50; N, 8.00. Calcd for $C_{88}H_{74}Cl_2Cu_3N_{12}O_{17}S_4 \cdot 4H_2O \cdot 2MeOH$: C, 51.53; H, 4.32; N, 8.01.

Example 7

Synthesis of Copper-64 Complexes of L3-L7

All copper-64 complexes were generated in situ and used in solution per the following procedure: $^{64}$Cu was produced from enriched $^{64}$Ni by the $^{64}$Ni(p,n)$^{64}$Cu reaction using a CS-15 biomedical cyclotron (Cyclotron Corporation, Berkeley, Calif.) at the Mallinckrodt Institute of Radiology, Washington University School of Medicine. Obtained purified stock solution of $^{64}$CuCl$_2$ in 0.05 M HCl was diluted in 0.1 M ammonium acetate (pH 5.5) for radiolabeling. About 1 mCi of $^{64}$Cu in 0.1M ammonium acetate (pH 5.5) was added to a reaction vial containing 0.01-0.05 μmol of a bifunctional compound (selected from L3-L7). The final volume was adjusted to 100 μL and vortexed for 10-15 seconds. Reactions were incubated on a thermomixer at 80° C. for 15 min. Labeling efficiency and radiochemical purity were determined using radio-high performance liquid chromatography (radio-HPLC, Agilent 1200) on a C18 column (Phenomenex Kinetex HPLC column, 150×4.6 mm I.D.) The mobile phase consisted of water (0.1% TFA) (A) and acetonitrile (0.1% TFA) (B) with a gradient of 0-100% B over 20 min and elution was run for 15 min using a flow rate of 1 mL/min. A radiochemical yield of greater than 95% was achieved for all compounds and the copper-64 labeled compounds were used without further purification.

Example 8

X-Ray Crystallography of Metal Complexes

The copper complexes of L4 and L7 were characterized by X-ray crystallography. Suitable crystals of appropriate dimensions were mounted in a Bruker Kappa Apex-II CCD X-Ray diffractometer equipped with an Oxford Cryostream LT device and a fine focus Mo Kα radiation X-Ray source ($\lambda$=0.71073 Å). Preliminary unit cell constants were determined with a set of 36 narrow frame scans. Typical data sets consist of combinations of $\bar{\omega}$ and $\phi$ scan frames with a typical scan width of 0.5° and a counting time of 15-30 seconds/frame at a crystal-to-detector distance of ~4.0 cm. The collected frames were integrated using an orientation matrix determined from the narrow frame scans. Apex II and SAINT software packages (*Bruker Analytical X-Ray*, Madison, Wis., 2008) were used for data collection and data integration. Final cell constants were determined by global refinement of reflections from the complete data set. Data were corrected for systematic errors using SADABS (*Bruker Analytical X-Ray*, Madison, Wis., 2008). Structure solutions and refinement were carried out using the SHELXTL-PLUS software package (Sheldrick, G. M. (2008), *Bruker-SHELXTL, Acta Cryst. A*64, 112-122). The structures were refined with full matrix least-squares refinement by minimizing $\Sigma w(Fo^2-Fc^2)^2$. All non-hydrogen atoms were refined anisotropically to convergence. All H atoms were added in the calculated position and were refined using appropriate riding models (AFIX $m^3$).

Figure 3:
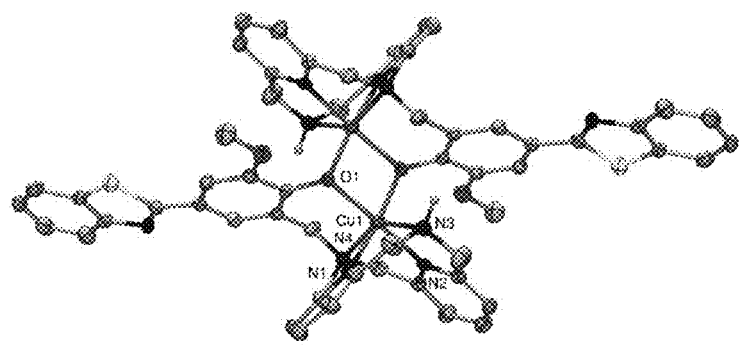
FIG. 3 shows an ORTEP plot of the Cu complex of L4 at 30% probability level. Perchlorate anions and hydrogen atoms are omitted for clarity.

Single crystals of the Cu complex of L4 were grown from a MeCN-Et$_2$O solution. FIG. 3 shows the ORTEP plot of the Cu complex of L4 ([(L4)Cu$^{II}$]$_2$(ClO$_4$)$_2$) at 30% probability level, with the perchlorate anions and hydrogen atoms omitted for clarity. The complex consists of a discrete centrosymmetric [(L4)Cu$^{II}$]$_2$ unit where two phenolates are acting as bridging groups between the two Cu centers. Each Cu$^{II}$ exhibits a distorted octahedral geometry. The two bridging oxygen atoms from the deprotonated pendant phenol groups, the two pyridyl nitrogen atom (N1), and the two amine nitrogen atoms complete the octahedral geometry around each Cu. The two bridging phenolate oxygen are bound asymmetrically to Cu$^{II}$ at distances of 2.002(3) and 1.995(3) Å, respectively, and the two Cu$^{II}$ centers are separated by 3.125 Å.

Figure 4:
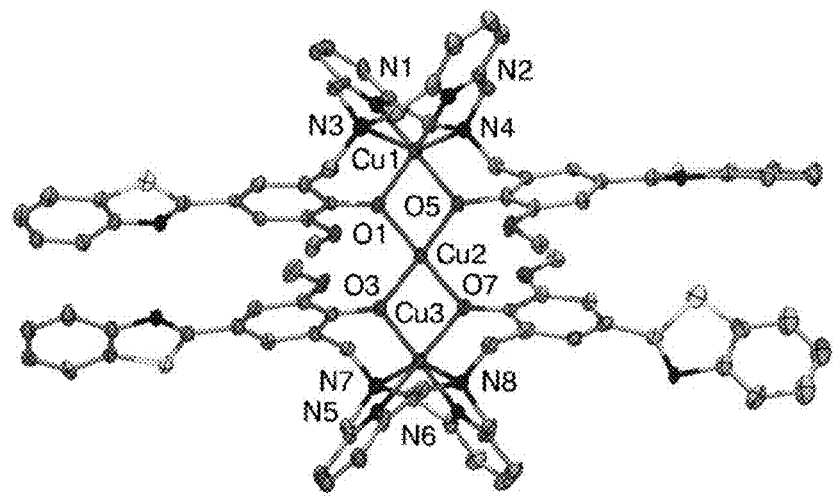
FIG. 4 shows an ORTEP plot of the Cu complex of L7 at the 30% probability level. Perchlorate anions and hydrogen atoms are omitted for clarity.

Single crystals of the L7-Cu complex of L7 were obtained from slow evaporation of a MeOH solution. FIG. 4 shows the ORTEP plot of the Cu complex of L7 ([(L7)Cu$^{II}$]) at the 30% probability level, with the perchlorate anions and hydrogen atoms are omitted for clarity. The molecular structure suggests a trinuclear complex in which a central Cu ion is situated between two L7-Cu units. The two terminal Cu centers are bound to four nitrogen atoms and two phenolate oxygen atoms in an octahedral geometry. The Cu—N distances are in the range of 1.977-2.323 Å.

Example 9

Acidity Constant Determination

Figure 1:
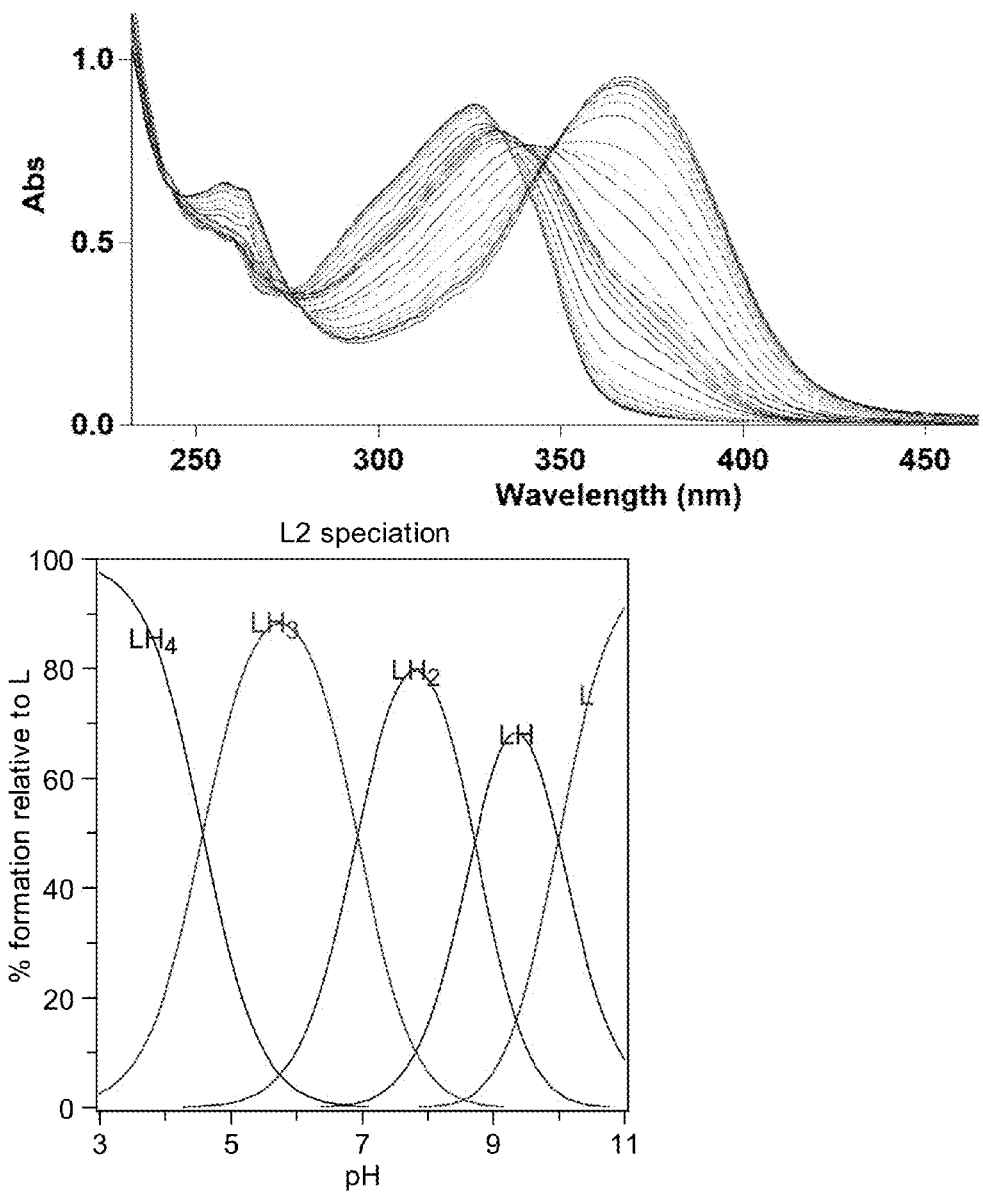
FIG. 1 shows a variable pH (pH 3-11) UV-vis spectra of L3 ([L3]=50 μM, 25° C., I=0.1 M NaCl) and species distribution plot created by the program HYSS2009.

UV-vis pH titrations were employed to determine the acidity constants of compounds L3-L7 and the stability constants of their Cu$^{2+}$ complexes. For acidity constants, solutions of the bifunctional compound (50 μM, 0.1 M NaCl, pH 3) were titrated with small aliquots of 0.1 M NaOH at room temperature. At least 30 UV-vis spectra were collected in the pH 3-11 range (FIG. 1). Due to the limited solubility of compounds in water, methanol, or dimethyl sulfoxide, stock solutions (10 mM) were used and titrations were performed in a methanol-water mixture in which methanol did not exceed 20% (v:v).

TABLE 1

| pK$_a$ Values for L3-L7 | | | | | |
|---|---|---|---|---|---|
|  | L3 | L4 | L5 | L6 | L7 |
| [HL1]$^-$/[L1]$^-$ (pKa4) | 9.34 | 10.14 | 9.60 | 9.98 | 10.65 |
| [H$_2$L1]$^+$/[HL1] (pKa3) | 8.27 | 9.34 | 8.02 | 8.71 | 8.22 |
| [H$_3$L1]$^{+2}$/[H$_2$L1]$^+$ (pKa2) | 6.35 | 7.84 | 5.61 | 6.93 | 7.39 |
| [H$_4$L1]$^{3+}$/[H$_3$L1]$^{2+}$ (pKa1) | 3.78 | 5.14 | 4.80 | 4.57 | 4.35 |

The highest pK$_a$ value was assigned to the phenol group and other three pK$_a$ values were assigned to the pyridine and amine groups. These pKa values predict what major species are present in solution at different pH values and suggest the compounds are stable in over the entire pH range typically employed in biological applications. These acidity constants were also needed for the calculation of the stability constants for the corresponding metal complexes.

Example 10

Stability Constant Determination

Similar spectrophotometric titrations were performed to determine the stability constants and solution speciation of Cu$^{2+}$ with L3-L6. Stability constants were determined by titrating solutions of the compounds and equimolar amounts of Cu(ClO$_4$)$_2$.6H$_2$O (50 μM or 0.5 mM) with small aliquots of 0.1 M NaOH at room temperature. At least 30 UV-vis spectra were collected in the pH 3-11 range (FIG. 2). The acidity and stability constants were calculated using the HypSpec computer program (Protonic Software, UK, Gans, P.; Sabatini, A.; Vacca, A. *Ann. Chim.* 1999, 45). Speciation plots of the compounds and their metal complexes were calculated using the program HySS2009 (Protonic Software, UK) (Alderighi, L. *Coord. Chem. Rev.* 1999, 184, 311). The data obtained for the Cu complexes of L3-L6 were fitted using a model suggesting the formation of a protonated complex at pH values below ~4, and a neutral complex at higher pH values. The data obtained for the Cu complex of compound L7 could not be fit satisfactorily using a reasonable model, most likely due to a multinuclear complex formation, as observed by X-ray crystallography.

TABLE 2

Stability constants$^a$ of the Cu$^{2+}$ complexes of L3-L6, as determined by pH-spectrophotometric measurements and calculated pM (–log[M]$_{free}$)

| Reaction | L3 | L4 | L5 | L6 |
|---|---|---|---|---|
| M$^{2+}$ + HL = [MHL]$^{+2}$ | — | 2.881 | 4.008 | 3.012 |
| M$^{2+}$ + L$^-$ = [ML]$^+$ | 31.96(60) | 27.093 | 27.224 | 30.098 |
| [ML(H$_2$O)]$^{+1}$ = [ML(OH)] + H$^+$ | 10.14(60) | | | |

$^a$The stability constants correspond to following reactions: [ML1]/[ML1(OH)]$^-$ (logβ$_{-1}$), [MHL1]$^+$/[ML1] (logβ$_1$), [MH$_2$L1]$^{+3}$/[MHL1]$^{+2}$ (logβ$_2$).

For a better comparison of the Cu$^{2+}$ binding affinities of these compounds, pCu (i.e. –log [Cu]$_{free}$) values are presented in Table 3. Interestingly, the pCu values of compounds with a macrocyclic metal binding pocket are significantly higher than non-macrocyclic compounds and standard chelators like diethylene triamine pentaacetic acid (DTPA). Overall, these results show that compounds L3-L7 are suitable as $^{64}$Cu chelating agents.

TABLE 3

Calculated pCu (–log[Cu]$_{free}$) for a solution containing a 1:1 solution of bifunctional compound and metal ion ([Cu$^{2+}$]$_{tot}$ = [chelator]$_{tot}$ = 50 μM).

| | L3 | L4 | L5 | L6 | DTPA |
|---|---|---|---|---|---|
| pH 6.6 | 12.77 | 11.66 | 11.49 | 12.01 | 9.3 |
| pH 7.4 | 13.27 | 13.47 | 12.33 | 14.14 | 10.1 |

Example 11

Electrochemical Studies

Figure 12:
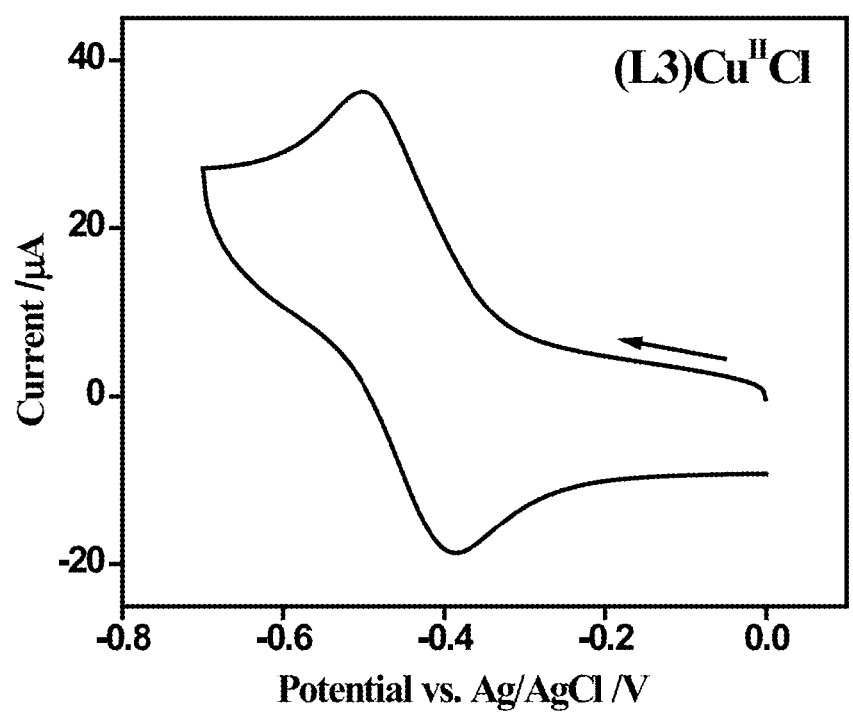
FIG. 12 shows a cyclic voltammogram of the Cu complex of L3 in 1:1 MeCN—H$_2$O with 0.1 M NaOAc at 100 mV/s scan rate.
Figure 13:
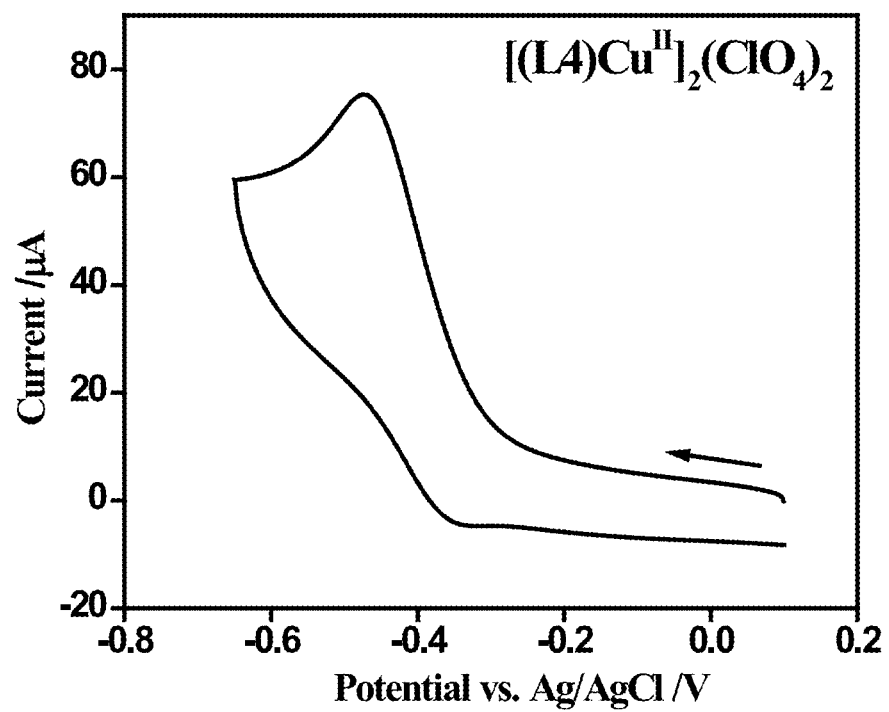
FIG. 13 shows a cyclic voltammogram of the Cu complex of L4 in 1:1 MeCN—H$_2$O with 0.1 M NaOAc at 100 mV/s scan rate.

A possible drawback of the Cu complexes utilized as radiopharmaceuticals is the possibility of demetalation upon the reduction from the Cu(II) to the Cu(I) oxidation state. Determination of the reduction potentials of these complexes using cyclic voltammetry (CV) can be used to evaluate their stability to reduction. Cyclic voltammograms of the isolated Cu complexes were determined in a 1:1 H$_2$O-MeCN solution, using a three-electrode setup consisting of a reference Ag/AgCl electrode, a platinum wire auxiliary electrode, and a glassy carbon working electrode. A 2 mM solution of the Cu$^{2+}$ complexes of the compounds in MeCN was mixed with equal volume of water (0.2 M sodium acetate electrolyte). The electrochemical measurements were performed under a blanket of nitrogen, and the analyzed solutions were deaerated by purging with nitrogen. Between each scan the working electrode was cleaned by polishing on alumina, cleaned with water and methanol. Cyclic voltammograms with sweep rate ranging from 100 to 1000 mV s$^{-1}$ were recorded in the voltage range +1200 to –1200 mV. All potential values are reported relative to the Ag/AgCl reference electrode in aqueous 3M NaCl unless otherwise noted. Representative cyclic voltammogram of (L3)Cu$^{II}$Cl and [(L4)Cu$^{II}$]$_2$(ClO$_4$)$_2$ are shown in FIG. 12 and FIG. 13, respectively. The Cu complexes of compounds L5, L6, and L7 show similar cyclic voltammograms (data not shown). All reduction potentials are in the range of –490 mV to –920 mV, similar to other compounds that have been employed in $^{64}$Cu radiolabeling (Esteves, C. V. et al. *Inorganic Chemistry*, 2013, 52, 5138; and Roger, M. et al. *Inorganic Chemistry*, 2013, 52, 5246).

Example 12

Amyloid β Peptide Experiments

Aβ monomeric films were prepared by dissolving commercial Aβ$_{42}$ (or Aβ$_{40}$ for Aβ fibril binding studies) peptide (Keck Biotechnology Resource Laboratory, Yale University) in hexafluoroisopropanol (HFIP) (1 mM) and incubating for 1 hour at room temperature (Klein, W. L. *Neurochemistry International* 2002, 41, 345). The solution was then aliquoted out and evaporated overnight. The aliquots were vacuum centrifuged and the resulting monomeric films stored at –80° C. Aβ fibrils were generated by dissolving monomeric Aβ films in dimethyl sulfoxide (DMSO), diluting into the appropriate buffer, and incubating for 24 hours at 37° C. with continuous agitation (final DMSO concentration was <2%). For metal-containing fibrils, the corresponding metal ions were added before the initiation of the fibrilization conditions. For inhibition studies, bifunctional compounds (50 μM, DMSO stock solutions) were added to Aβ solutions (25 mM) in the absence or presence of metal salt (CuCl$_2$ 25 μM) and incubated for 24 h at 37° C. with constant agitation.

Example 13

Fluorescence Measurements

All fluorescence measurements were performed using a SpectraMax M2e plate reader (Molecular Devices). For ThT fluorescence studies, samples were diluted to a final concentration of 2.5 μM Aβ in phosphate buffered saline (PBS) solution containing 10 μM ThT and the fluorescence measured at 485 nm ($\lambda_{ex}$=435 nm). For Aβ fibril binding studies, a 5 μM Aβ fibril solution was titrated with small amounts of compound and their fluorescence intensity measured ($\lambda_{ex}$/$\lambda_{em}$=350/450 nm). For ThT competition assays, a 2 μM Aβ fibril solution with 1 μM ThT was titrated with small amounts of compound and the ThT fluorescence measured ($\lambda_{ex}$/$\lambda_{em}$=435/485 nm).

In the direct fluorescence assay, the increase in the compound fluorescence intensity was monitored in presence of Aβ fibrils. A significant increase in the intrinsic fluorescence was only observed for L3, corresponding to a K$_d$ of ~575±90 nM (FIG. 5, graph (a)). In addition, fluorescence competition assays were employed to determine the binding affinity of compounds L4-L7 toward the Aβ fibrils. In this assay, a fixed concentration of Aβ fibrils and ThT is titrated by adding various amounts of competitor ligand (0 to 10 μM) and monitoring the decrease in ThT fluorescence. Compound L3 exhibits a K$_i$ value of 175±50 nM (FIG. 5, graph (b)), while compounds L4 and L5 exhibit stronger affinities corresponding to $K_i$ values of 30±10 nM and 40±10 nM, respectively (FIG. 6, graphs (a) and (b)). L6 and L7 show lower affinities with $K_i$ values of 325±40 and 585±50 nM (FIG. 6, graphs (a) and (b)). Overall, all compounds L4-L7 show affinities for Aβ fibrils that are stronger than the amyloid-binding dye Thioflavin T (ThT).

Example 14

Epifluorescence Microscopy

The emission properties of compounds L3-L7 were employed to determine the binding affinity of these compounds toward amyloid plaques in brain sections from Tg2576 APP transgenic mice by epifluorescence microscopy. APP transgenic and wild type mouse brain sections were carefully selected and removed from the cryoprotectant solution using a phosphate buffered saline (PBS) solution with 0.1% Tween-20. After washing them three timed with PBS, they were incubated for 45 minutes in a solution of 10:1 (v/v) compound: Congo Red—a known amyloid-binding fluorescent dye. After that, brain sections were washed for 5 min each in PBS, PBS-EtOH (1:1), and PBS again. Vectashield mounting media (H1000) was used to prevent fading and photobleaching. Images were taken on a Nikon Eclipse 80i Microscope.

Figure 10:
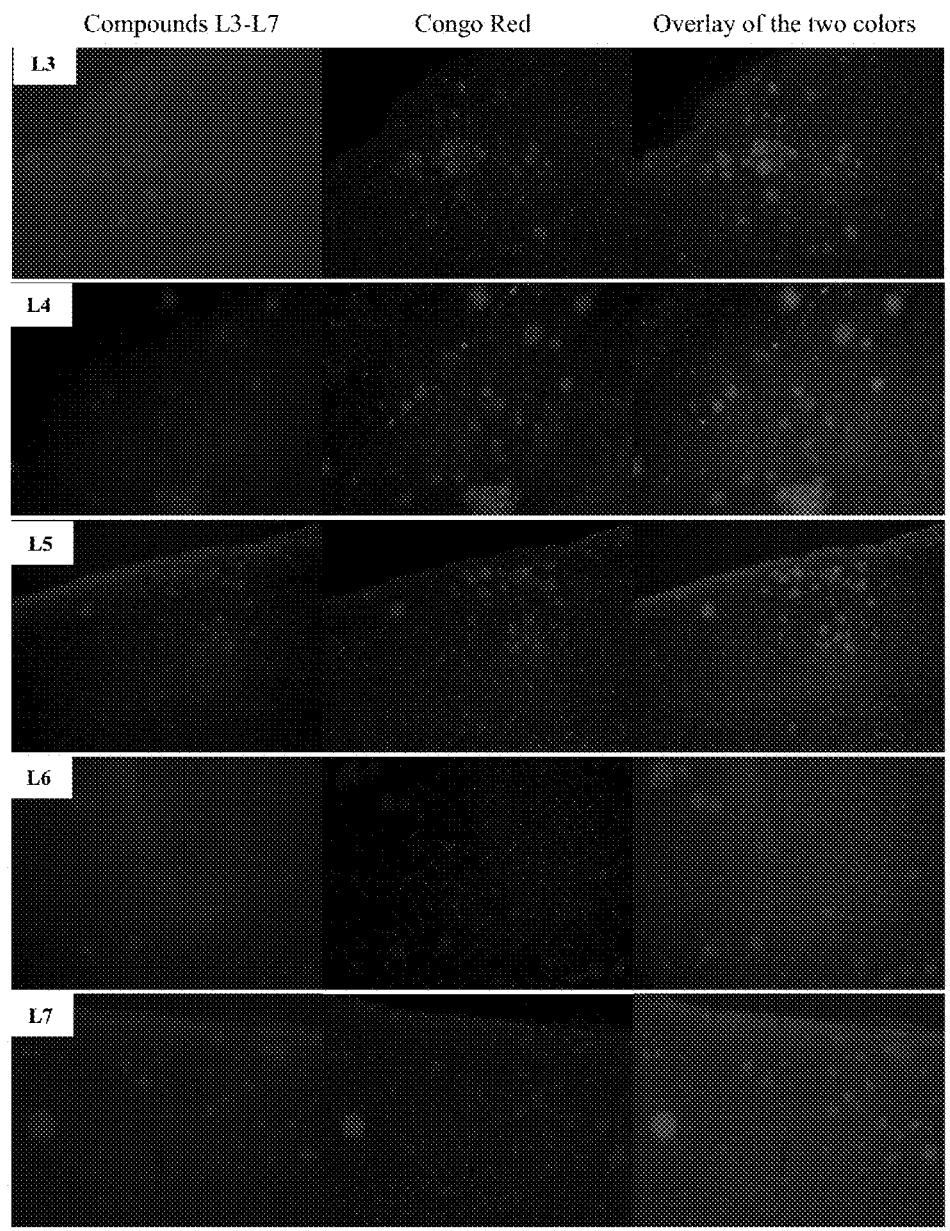
FIG. 10 shows an epifluorescence images of brain sections incubated with compounds L3-L7 (column 1, rows 1-5, respectively, using blue light excitation), Congo Red—a known amyloid-binding fluorescent dye (column 2, using red light excitation), and overlay of the two excitation colors showing co-localization of compounds L3-L7 and Congo Red (column 3, rows 1-5, respectively.

All compounds L3-L7 emit a blue light when bound to amyloid plaques (FIG. 10, column 1). Binding to the plaques was confirmed by co-localization with Congo-red (FIG. 10, column 3), a dye known for binding to amyloid plaques (FIG. 10, column 2). This data clearly show that these compounds bind to amyloid plaques and can be used for fluorescence imaging of amyloid plaques in-vivo. In addition, compounds L3-L7 seem to bind to a larger number of Aβ species compared to Congo Red (as show in FIG. 10 for the overlay of the two colors), suggesting that these compounds likely bind to various Aβ species, not only to amyloid fibrils.

Example 15

Transmission Electron Microscopy (TEM)

The ability of L3-L7 to inhibit amyloid fibril formation was also investigated. The monomeric $A\beta_{42}$ peptide was incubated with compounds L3-L7 for 24 h at 37° C. and analyzed by TEM and native gel electrophoresis/Western blotting. Glow-discharged grids (Formar/Carbon 300-mesh, Electron Microscopy Sciences) were treated with Aβ samples (25 µM, 5 µL) for 2-3 minutes at room temperature. Excess solution was removed using filter paper and grids were rinsed twice with water (5 µL). Grids were stained with uranyl acetate (1% w/v, water, 5 µL) for 1 minute, blotted with filter paper, and dried for 15 minutes at room temperature. Images were captured using a FEI G2 Spirit Twin microscope (60-80 kV, 6500-97000× magnification).

Figure 7:
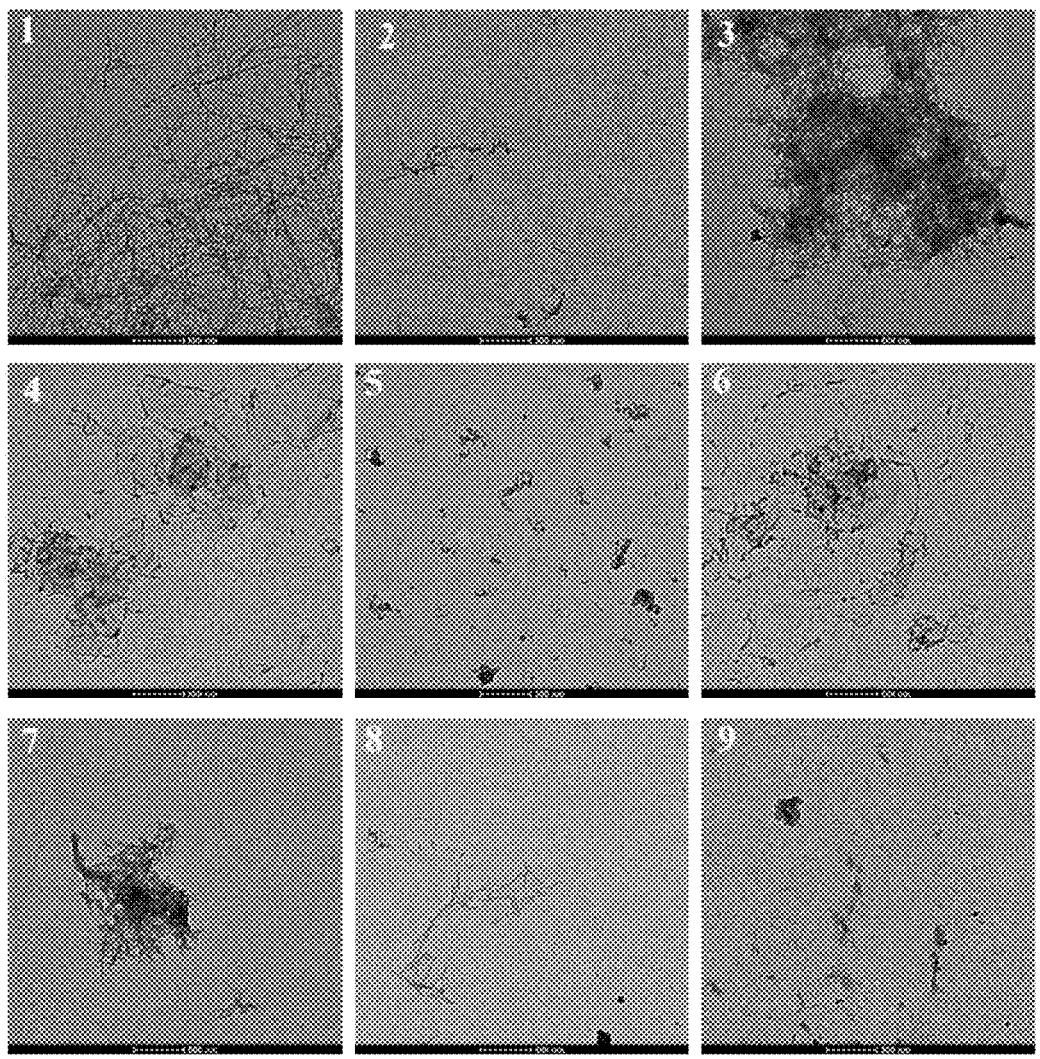
FIG. 7 shows TEM images of inhibition of Aβ$_{42}$ aggregation by L3 and L4. Conditions are: ([Aβ]=25 μM, [M$^{2+}$]=25 μM, [compound]=25 μM, 24 h, 37° C.). All scale bars represent 500 nm. Panels: 1. Aβ; 2. Aβ+Cu; 3. Aβ+Zn; 4. Aβ+L3; 5. Aβ+L3+Cu; 6. Aβ+L3+Zn; 7. Aβ+L4; 8. Aβ+L4+Cu; 9. Aβ+L4+Zn.
Figure 8:
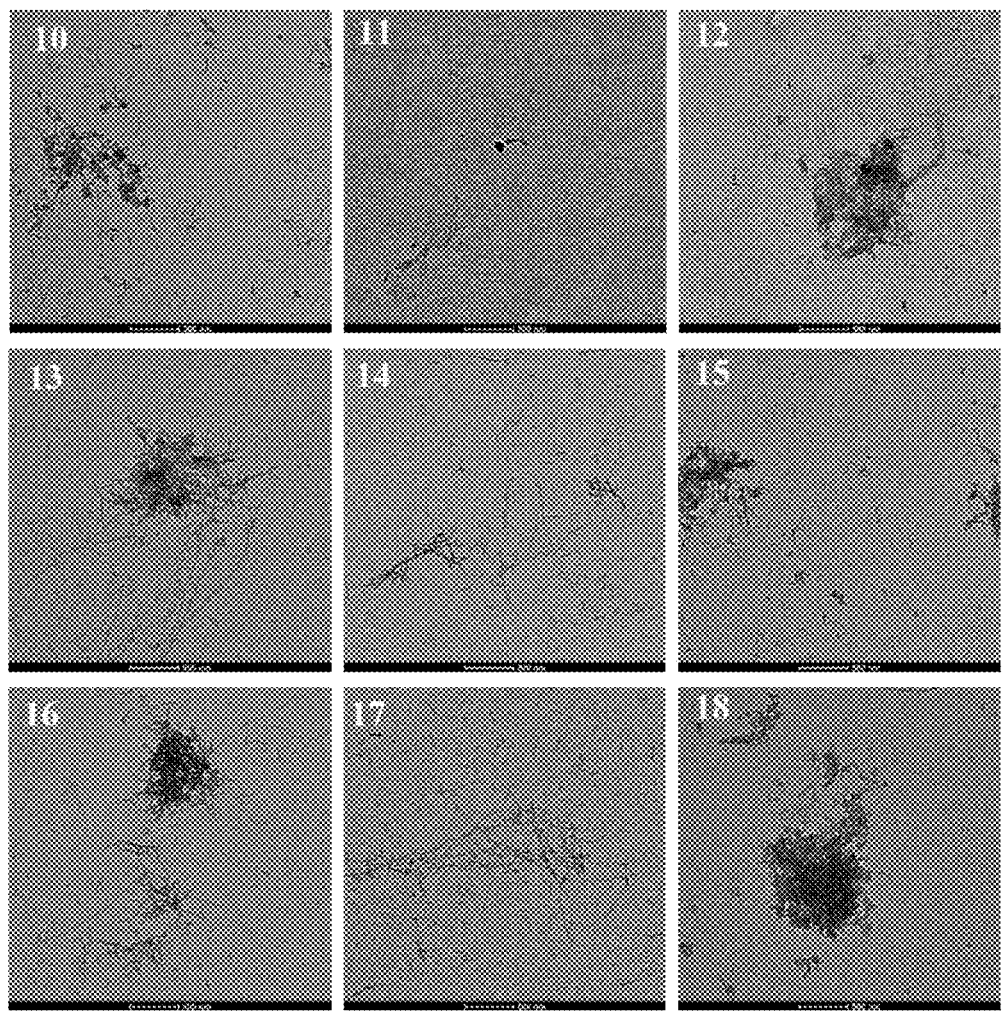
FIG. 8 shows TEM images of inhibition of Aβ$_{42}$ aggregation by L5, L6 and L7. Conditions are: ([Aβ]=25 μM, [M$^{2+}$]=25 μM, [compound]=25 μM, 24 h, 37° C.). All scale bars represent 500 nm. Panels: 10. Aβ+L5; 11. Aβ+Cu+L5; 12. Aβ+Zn+L5; 13. Aβ+L6; 14. Aβ+L6+Cu; 15. Aβ+L6+Zn; 16. Aβ+L7; 17. Aβ+L7+Cu; 18. Aβ+L5+Zn.

FIG. 7 shows TEM images of inhibition of $A\beta_{42}$ aggregation by L3 and L4, and FIG. 8 shows TEM images of inhibition of $A\beta_{42}$ aggregation by L5, L6 and L7. TEM analysis is used for the characterization of the larger, insoluble Aβ aggregates that cannot be analyzed by gel electrophoresis. $A\beta_{42}$ forms large fibrils in 24 h of incubation at 37° C. TEM images of inhibition experiment suggest that all the compounds L3-L7 shows a good inhibition of fibrilization process both in absence and in presence of metal ions, (FIGS. 7 and 8).

Example 16

Native Gel Electrophoresis and Western Blotting

Western Blot analysis was done in order to reveal the presence of smaller, soluble Aβ aggregates and their molecular weight distribution under these conditions. All gels, buffers, membranes, and other reagents were purchased from Invitrogen and used as directed except where otherwise noted. Samples were separated on 10-20% gradient Tris-tricine mini gels. The gel was transferred to a nitrocellulose membrane in an ice bath and the protocol was followed as suggested except that the membrane was blocked overnight at 4° C. After blocking, the membrane was incubated in a solution of 6E10 anti-Aβ primary antibody (Covance) for 3 hours. Invitrogen's Western Breeze Chemiluminescent kit was used to visualize the bands. An alkaline-phosphatase anti-mouse secondary antibody was used, and the protein bands were imaged using a FUJIFILM Luminescent Image Analyzer LAS-1000CH.

Native gel/Western blot analysis suggests that the compounds L3-L7 reduce the formation of higher order oligomers (FIG. 9). Moreover, in the presence of metal ions, the formation of higher order oligomers is completely inhibited. Importantly, the compounds L3-L7 do not lead to enhanced formation of neurotoxic soluble Aβ species, as observed previously for other compounds (Sharma et al., J. Am. Chem. Soc., 2012, 134: 6625-6636).

Example 17

Binding Assay with Copper-64 Labeled Metal Complexes

In addition to the Aβ binding affinity studies of compounds L3-L7 (FIG. 5), we have also investigated the affinity of the corresponding $^{64}$Cu-labeled complexes toward Aβ fibrils. To perform binding assay, 5 µg of $A\beta_{40}$ fibrils in a volume of 100 µL binding buffer [10 mM HEPES, 5 mM $MgCl_2$, 1 mM EDTA, 0.1% BSA, 10 µg/ml leupeptin, 10 µg/ml pepstatin, 0.5 µg/ml aprotinin, and 200 µg/ml bacitracin, pH 7.4] were applied to 0.1% polyethyleneimine-pretreated wells of a 96-well Multiscreen Durapore filtration plate (Millipore Corp., Bedford, Mass.) via vacuum manifold aspiration. These were performed in triplicates for each sample. The wells were washed three times with wash buffer (10 mM HEPES, 1 mM EDTA, 5 mM $MgCl_2$, 0.1% BSA). After the addition of 5 µg of $A\beta_{40}$ fibrils to each well, 0 µg of block, 10 µg of BTZ-2 (4-hydroxy-phenylbenzothiazole, used as blocking compound) in a volume of 10 µL of binding buffer was added to triplicate wells. To each well, approximately 500,000 CPM of $^{64}$Cu labeled compound was added in a volume of 100 µL to triplicate wells. The plate was incubated at room temperature for 1 hour on a shaker, and then the wells were washed twice with wash buffer. The membranes were allowed to dry, removed, and placed in separate tubes for determination of bound radioactivity. The radioactivity was counted using a Beckman Gamma 8000 counter containing a sodium iodide (NaI) crystal (Beckman Instruments, Inc., Irvine, Calif.). The data were plotted as bar charts using Microsoft Excel software package. These results strongly suggest that the $^{64}$Cu complexes of compounds L3-L7 also have high binding affinity for Aβ fibrils.

Example 18

Autoradiography Imaging of Mouse Brain Sections

Alzheimer and wild type mouse brain sections were carefully selected and removed from the cryoprotectant solution using a phosphate buffer in saline (PBS) with 0.1% tween-20. Brain sections were mounted on an image slide (Leica, Cryo-Jane, CSFA adhesive slides) and washed three times using 100% PBS. About 25 µCi of $^{64}$Cu labeled compound in a 100

μL total volume was added to completely cover the brain section and incubated at room temperature for 1 hour. Once the incubation was completed, brain sections were washed using PBS with five×1 minute cycles and briefly air-dried. Imaging slides were mounted onto storage phosphor screen cassettes (GE Healthcare, 20×25 cm), exposed for 3 minutes, and then screens were scanned using a Storm 840 phosphor image plate scanner. The resulting scanned images were processed using ImageQuant 5.2 software.

Figure 11:
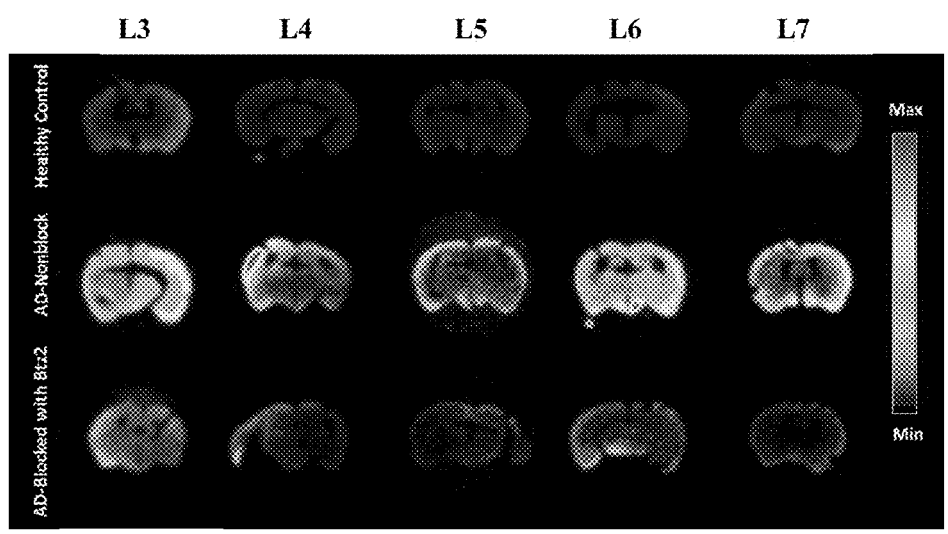
FIG. 11 shows autoradiography images of brain sections incubated with $^{64}$Cu-labeled compounds L3-L7. Brain sections from age-matched wild type mice controls are shown in row 1, brain sections from APP transgenic mice are shown in rows 2 and 3. For the blocking study (row 3), 4-hydroxybenzothiazole (BTZ) was used as a non-Cu binding blocking agent with nanomolar affinity for Aβ fibrils.

By comparison to the wild type, healthy brain sections, much more amyloid plaques were observed in the brain sections of APP transgenic mouse brain sections (FIG. 11, first and second row). Importantly, the $^{64}$Cu labeled compounds L3-L7 revealed an increased autoradiography intensity corresponding to the presence of the amyloid plaques (FIG. 11, second row). These results were further supported by blocking experiments. When the binding sites on the amyloid plaques were blocked by a strong amyloid binding compound 4-hydroxybenzothiazole (BTZ2), a marked decreased autoradiography intensity were observed, supporting a specific binding of the $^{64}$Cu labeled compounds for the amyloid plaques. Thus, these autoradiography data clearly indicate that $^{64}$Cu complexes of compounds L3-L7 exhibit the ability to image the amyloid plaques in vivo.

Example 19

Alamar Blue Assay

Cell toxicity studies were employed to evaluate the cytotoxicity of compounds L3-L7. Mouse neuroblastoma Neuro2A (N2A) cell lines were purchased from the American Type Culture Collection (ATCC). Cells were grown in DMEM/10% FBS, which is the regular growth media for N2A cells. N2A cells were plated to each well of a 96 well plate (2.5×10$^4$/well) with DMEM/10% FBS. The media was changed to DMEM/N2 media 24 h later. After 1 hour, the reagents (20 μM Aβ$_{42}$ species, compounds, and metals) were added. Due to the poor solubility of compounds in water or media, the final amount of DMSO used was 1% (v:v). After an additional incubation of 40 h, the Alamar blue solution was added in each well and the cells were incubated for 90 min at 37° C. Absorbance was measured at 570 nm (control OD=600 nm). These studies show that compounds L3-L7 become toxic only at micromolar concentrations, which are much higher than what is needed for PET imaging applications (i.e., nanomolar concentrations).

Example 20

Evaluation of Biodistribution and Brain Uptake of $^{64}$Cu-Radiolabeled Compounds Biodistribution studies were conducted in wild type CD-1 female mice (Charles River Laboratories) of age 5-7 weeks weighing 25.4±1.4 g. The injection dose was prepared by diluting to a 90% saline solution. The uptake of compounds was evaluated in mice (L3 and L6, n=7; L4, L5, and L7, n=3) that were injected via the tail vein with 0.22-0.37 MBq (6-10 μCi) of each compound per animal in 100 μL saline. After each time points (2, 60, and 240 min), mice were anesthetized with 1-2% isoflurane and sacrificed by cervical dislocation. Brain, blood, kidney, liver and other organs of interest were harvested and amount of radioactivity in each organ was counted on a gamma counter containing a NaI crystal. The data was corrected for radioactive decay and percent injected dose per gram (% ID/g) of tissue was calculated. All samples were calibrated against a known standard. Quantitative data were processed by Prism 6 (GraphPad Software, v 6.03, La Jolla, Calif.) and expressed as Mean±SEM. Statistical analysis performed using one-way analysis of variance and Student's t test. Differences at the 95% confidence level (p<0.05) were considered statistically significant.

Figure 14:
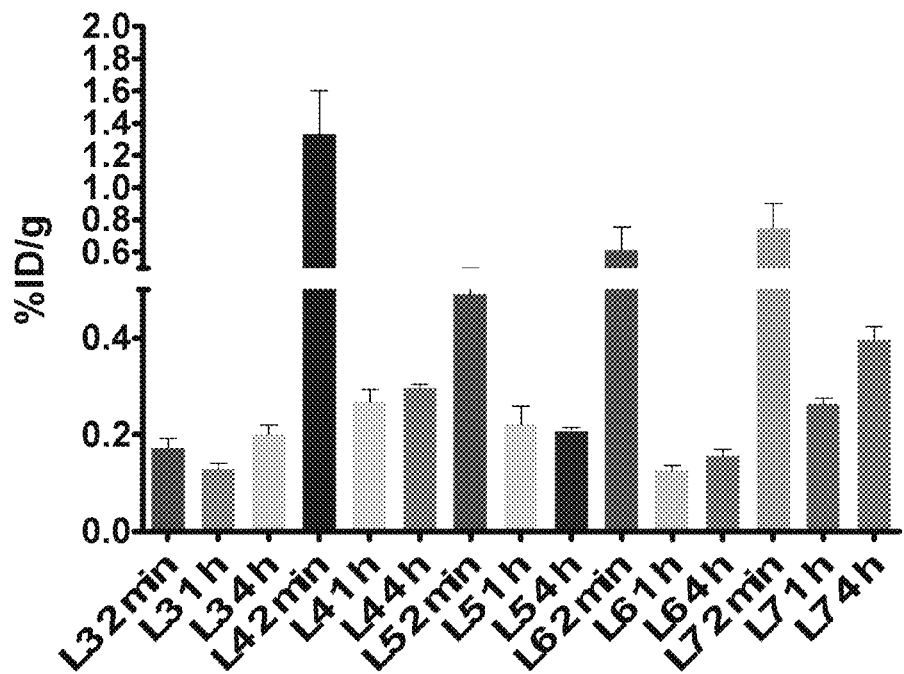
FIG. 14 shows the results of an in vivo biodistribution study in CD-1 mice, showing that the $^{64}$Cu-radiolabeled compounds exhibit initial brain uptake, followed by rapid wash out from the WT mice.

FIG. 14 shows the results of this in vivo biodistribution study in CD-1 mice, showing that the $^{64}$Cu-radiolabeled compounds exhibit initial brain uptake, followed by rapid wash out from the WT mice.

Importantly, this in vivo biodistribution studies with injected in wild type mice show that these complexes, especially those of L4, L5, L6, and L7, exhibit higher initial brain uptake at 2 min, followed by rapid wash out from the brain of wild type mice (FIG. 14). These results show that the $^{64}$Cu-labeled compounds can cross the blood brain barrier and yet can be are rapidly cleared from the brain of mice that do not have amyloid plaques. This low accumulation in the brain of healthy mice is desired, such that a high contrast can be observed when the radiolabeled compound will bind specifically to amyloid aggregates in AD mice.

Example 21

Synthesis of Complex L8

A mixture of 4-bromoveratrole (1.3 g, 6 mmol), 4-acetoxystyrene (0.97 g, 6 mmol), triethanolamine (10 mL) and palladium acetate (13.5 mg) was stirred under N$_2$ at 100° C. for 48 h. After cooling, the mixture was quenched with 2N HCl (10 mL) for 2 h and extracted with ether (25 mL×4). The organic layer was dried with MgSO$_4$ and the solvent removed by rotary evaporation. The solid product (400 mg, 26% yield) was purified by silica gel column chromatography using ethyl acetate/hexane ratios from 1:9 to 1:1.

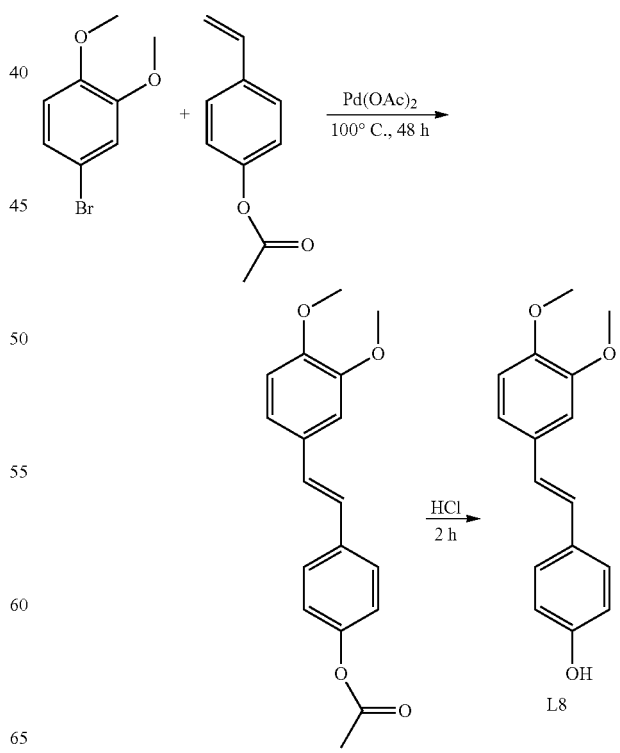

Example 21

Fluorescence Measurements

Figure 15:
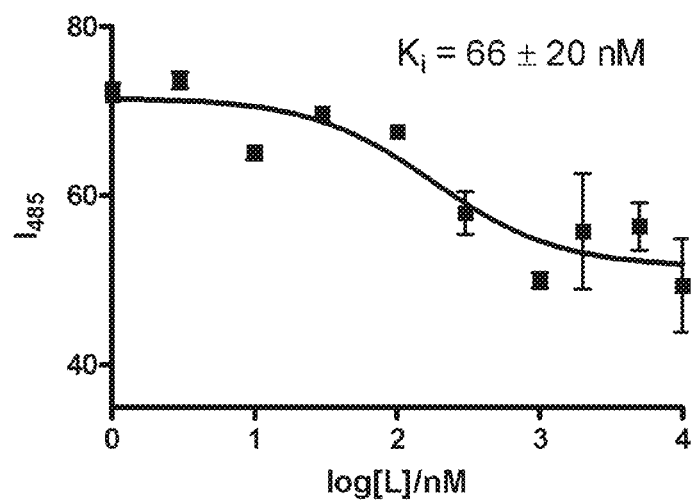
FIG. 15 shows a ThT fluorescence competition assay of L8 with ThT-bound Aβ$_{40}$ fibrils ([Aβ]=2 μM, [ThT]=1 μM).

Example 13 was repeated for L8. Compound L8 exhibits a $K_i$ value of 66±20 nM (FIG. 15) in the ThT fluorescence competition assay with ThT-bound $A\beta_{40}$ fibrils ([$A\beta$]=2 μM, [ThT]=1 μM). The amyloid binding data shown in FIG. 15 shows that the bis(methoxy)stilbene-phenol molecular framework characteristic of the compounds of Formula (V) exhibits strong binding affinity toward amyloid fibrils.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained. As various changes could be made in the above compositions and method without departing from the scope of the invention, it is intended that all matter contained in the above description and shown in the accompanying drawing[s] shall be interpreted as illustrative and not in a limiting sense.

Having described the invention in detail, it will be apparent that modifications and variations are possible without departing from the scope of the invention defined in the appended claims.

What is claimed is:

1. A compound of Formula (III) or a pharmaceutically acceptable salt thereof:

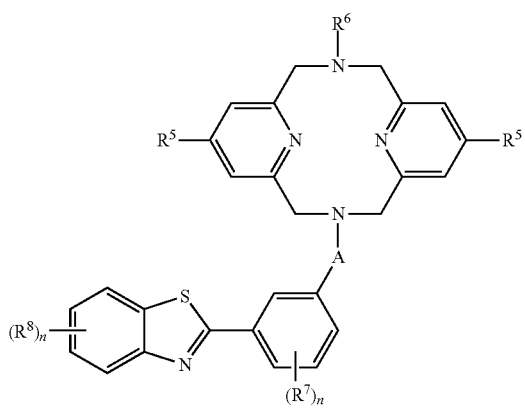

(III)

wherein
each $R^5$ is independently hydrogen, hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;
$R^6$ is hydrogen, substituted or unsubstituted $C_1$-$C_4$ alkyl, substituted or unsubstituted aryl, substituted or unsubstituted heteroaryl, substituted or unsubstituted $C_1$-$C_4$ alkylcarboxy, substituted or unsubstituted $C_1$-$C_4$ alkylamide, substituted or unsubstituted $C_1$-$C_4$ alkylester, or a moiety of Formula (IV):

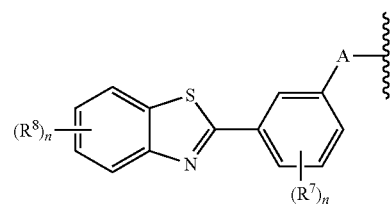

(IV)

each $R^7$ and $R^8$ of Formulas (III) and (IV) is independently hydroxy, halo, nitro, amino, substituted or unsubstituted $C_1$-$C_4$ alkyl, substituted or unsubstituted $C_1$-$C_4$ alkoxy, substituted or unsubstituted aryl, or substituted or unsubstituted heteroaryl;
each n in Formulas (III) and (IV) is independently 0 to 4, 0 to 3, 0 to 2, 1, or 0; and
each A in Formulas (III) and (IV) is independently $C_1$-$C_4$ alkylene, carbonyl, amide, thioamide, sulfonamide, urea, or carbamate.

2. The compound of claim 1 wherein:
each $R^5$ is independently hydrogen, hydroxy, halo, unsubstituted $C_1$-$C_4$ alkyl, or unsubstituted $C_1$-$C_4$ alkoxy;
$R^6$ is hydrogen, unsubstituted $C_1$-$C_4$ alkyl, unsubstituted $C_1$-$C_4$ alkylcarboxy, unsubstituted $C_1$-$C_4$ alkylamide, unsubstituted $C_1$-$C_4$ alkylester, or a moiety of Formula (IV);
each $R^7$ and $R^8$ of Formulas (III) and (IV) is independently hydroxy, unsubstituted $C_1$-$C_4$ alkyl, or unsubstituted $C_1$-$C_4$ alkoxy; and
each A in Formulas (III) and (IV) is independently $C_1$-$C_4$ alkylene.

3. The compound of claim 1 wherein:
each $R^5$ is independently hydrogen, halo, or unsubstituted $C_1$-$C_4$ alkoxy;
$R^6$ is hydrogen, unsubstituted $C_1$-$C_4$ alkyl, unsubstituted $C_1$-$C_4$ alkylcarboxy, unsubstituted $C_1$-$C_4$ alkylester, or a moiety of Formula (IV);
each $R^7$ and $R^8$ of Formulas (III) and (IV) is independently hydroxy, or unsubstituted $C_1$-$C_4$ alkoxy; and
each A in Formulas (III) and (IV) is independently methylene or ethylene.

4. The compound of claim 1 selected from the group consisting of:

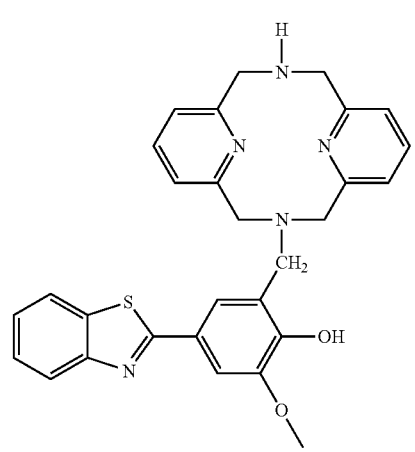

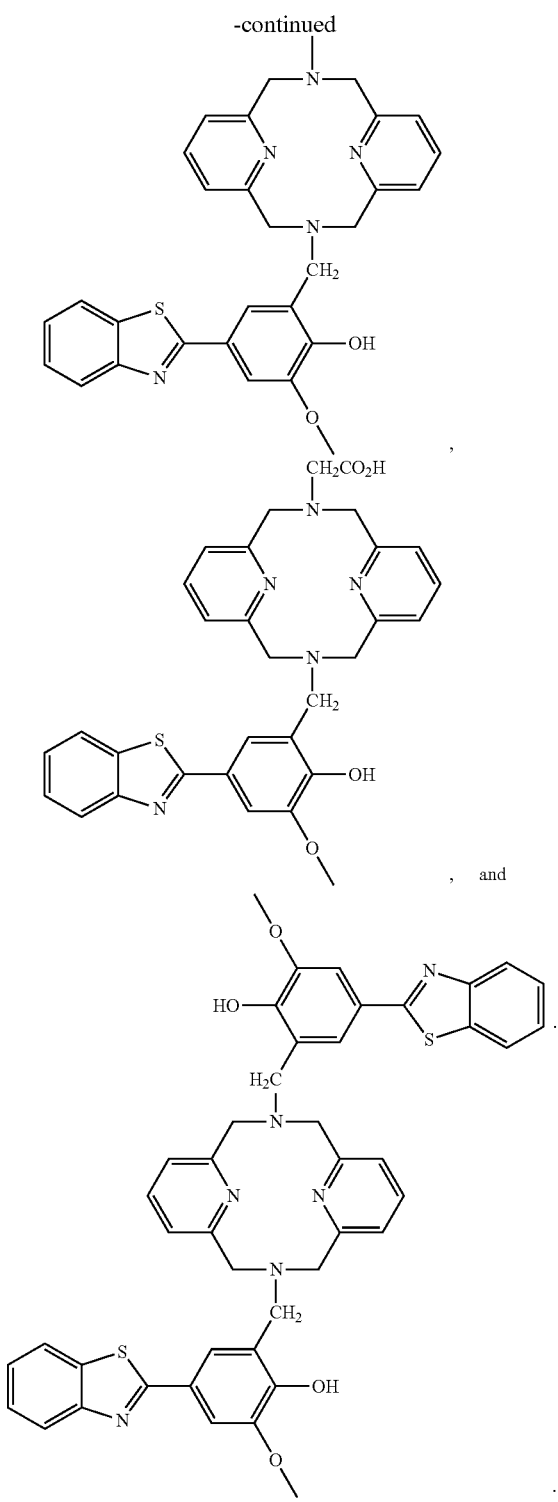

5. A metal radionuclide complex comprising a compound of claim 1 and a metal radionuclide.

6. The metal radionuclide complex of claim 5 wherein the metal radionuclide is a positron emitting isotope.

7. The metal radionuclide complex of claim 6 wherein the metal radionuclide is selected from the group consisting of technetium-99m (Tc-99m(=O)), gallium-66 (Ga-66), yttrium-86 (Y-86), zirconium-89 (Zr-89), cobalt-55 (Co-55), manganese-52 (Mn-52), copper-60 (Cu-60), copper-61 (Cu-61), copper-62 (Cu-62), and copper-64 (Cu-64).

8. A method of diagnosing or monitoring a β-amyloid disease in a subject comprising:

administering a radiopharmaceutical composition comprising a diagnostically effective amount of a metal radionuclide complex of claim 5 to the subject;

imaging the subject's brain by position emission tomography; and detecting the binding of the metal radionuclide complex to Aβ species.

9. The method of claim 8 wherein the radiopharmaceutical composition is administered at a dose of 10 μCi to 10 mCi.

10. The method of claim 8 wherein the β-amyloid disease is Alzheimer's disease.

11. The method of claim 8 wherein the β-amyloid disease is dementia with Lewy bodies (DLB), cerebral amyloid angiopathy (CAA), Down's syndrome, mild cognitive impairment, and posterior cortical atrophy (PCA).

12. The compound of claim 1 wherein each $R^5$ is independently hydrogen, hydroxy, halo, unsubstituted $C_1$-$C_4$ alkyl, or unsubstituted $C_1$-$C_4$ alkoxy.

13. The compound of claim 1 wherein each $R^5$ is independently hydrogen, halo, or unsubstituted $C_1$-$C_4$ alkoxy.

14. The compound of claim 1 wherein $R^6$ is hydrogen, unsubstituted $C_1$-$C_4$ alkyl, unsubstituted $C_1$-$C_4$ alkylcarboxy, unsubstituted $C_1$-$C_4$ alkylamide, unsubstituted $C_1$-$C_4$ alkylester, or a moiety of Formula (IV).

15. The compound of claim 1 wherein $R^6$ is hydrogen, unsubstituted $C_1$-$C_4$ alkyl, unsubstituted $C_1$-$C_4$ alkylcarboxy, unsubstituted $C_1$-$C_4$ alkylester, or a moiety of Formula (IV).

16. The compound of claim 1 wherein each $R^7$ and $R^8$ of Formulas (III) and (IV) is independently hydroxy, unsubstituted $C_1$-$C_4$ alkyl, or unsubstituted $C_1$-$C_4$ alkoxy.

17. The compound of claim 1 wherein each $R^7$ and $R^8$ of Formulas (III) and (IV) is independently hydroxy, or unsubstituted $C_1$-$C_4$ alkoxy.

18. The compound of claim 1 wherein each A in Formulas (III) and (IV) is independently $C_1$-$C_4$ alkylene.

19. The compound of claim 1 wherein each A in Formulas (III) and (IV) is independently methylene or ethylene.

* * * * *